(12) United States Patent
Golec et al.

(10) Patent No.: US 7,053,057 B2
(45) Date of Patent: May 30, 2006

(54) CASPASE INHIBITORS AND USES THEREOF

(75) Inventors: Julian M. C. Golec, Ashbury Swindon (GB); David Bebbington, Newbury (GB); Guy Brenchley, Grove Wantage (GB); Ronald Knegtel, Abingdon (GB); Michael Mortimore, Burford (GB)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 10 days.

(21) Appl. No.: 09/863,649

(22) Filed: May 23, 2001

(65) Prior Publication Data
US 2002/0061853 A1 May 23, 2002

Related U.S. Application Data

(60) Provisional application No. 60/206,362, filed on May 23, 2000, provisional application No. 60/217,006, filed on Jul. 10, 2000.

(51) Int. Cl.
*A61K 38/05* (2006.01)
*C07K 5/078* (2006.01)

(52) U.S. Cl. .............. 514/19; 435/1.1; 435/2; 435/374; 546/146; 546/147; 546/164; 546/169; 546/170; 546/226

(58) Field of Classification Search .......... 435/1.1, 435/1.2, 1.3, 2, 374, 431; 514/19; 546/146, 546/147, 164, 169, 170, 226
See application file for complete search history.

(56) References Cited

U.S. PATENT DOCUMENTS 5,866,545 A * 2/1999 Hagmann et al. ......... 514/18
6,045,990 A * 4/2000 Baust et al. ............ 435/1.1
6,136,834 A * 10/2000 Ohmoto et al. ......... 514/381

FOREIGN PATENT DOCUMENTS

| WO | WO 91/15577 | 10/1991 |
| WO | WO 99/18781 | 4/1999 |
| WO | WO 99/47154 | 9/1999 |

* cited by examiner

*Primary Examiner*—Jeffrey Edwin Russel
(74) *Attorney, Agent, or Firm*—Lisa A. Dixon; Vertex Pharmaceuticals Incorporated

(57) ABSTRACT

This invention provides caspase inhibitors having the formula:

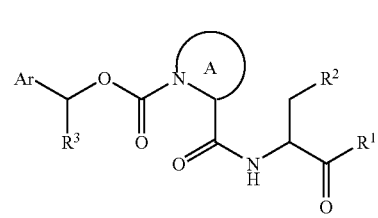

wherein Ring A is an optionally substituted piperidine, tetrahydroquinoline or tetrahydroisoquinoline ring; $R^1$ is hydrogen, $CHN_2$, R, or $-CH_2Y$; R is an optionally substituted group selected from an aliphatic group, an aryl group, an aralkyl group, a heterocyclic group, or an heterocyclylalkyl group; Y is an electronegative leaving group; $R^2$ is $CO_2H$, $CH_2CO_2H$, or esters, amides or isosteres thereof; Ar is an optionally substituted aryl group; and $R^3$ is hydrogen, an optionally substituted $C_{1-6}$ alkyl, $F_2$, CN, aryl or $R^3$ is attached to Ar to form an unsaturated or partially saturated five or six membered fused ring having 0–2 heteroatoms. The compounds are useful for treating caspase-mediated diseases in mammals.

38 Claims, No Drawings

CASPASE INHIBITORS AND USES THEREOF

This application claims the benefit of U.S. provisional patent application Ser. No. 60/206,362 filed May 23, 2000 and U.S. provisional patent application Ser. No. 60/217,006 filed Jul. 10, 2000.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283–1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97–R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequences primarily recognized by the caspases has been used to design caspase inhibitors. Reversible tetrapeptide inhibitors have been prepared having the structure $CH_3CO$—[P4]—[P3]—[P2]—$CH(R)CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149–155 (1997); Mjalli, et al., *Bioorg. Med. Chem. Lett.* 3, 2689–2692 (1993); Nicholson et al., *Nature* 376, 37–43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563–564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., *J. Clin. Invest.*, 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

The unsuitable pharmacological properties of the tetra- and tri-peptidic caspase inhibitors has brought about the development of natural and non-natural amino acid di-peptidic inhibitors of caspases.

WO 91/15577 and WO 93/05071 disclose peptide ICE inhibitors of the formula:

wherein Z is an N-terminal protecting group; $Q_2$ is 0 to 4 amino acids; and $Q_1$ is an electronegative leaving group. However, WO 91/15577 only reports these compounds to be active against caspase-1 and does not report activity against other caspases.

WO 99/18781 discloses dipeptide caspase inhibitors of the formula:

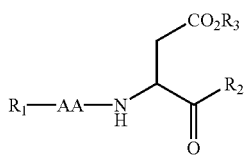

wherein $R_1$ is an N-terminal protecting group; AA is a residue of a natural α-amino acid, or β-amino acid; $R_2$ is H or $CH_2R_4$ where $R_4$ is an electronegative leaving group; and $R_3$ is alkyl or H.

WO 99/47154 discloses dipeptide caspase inhibitors of the formula:

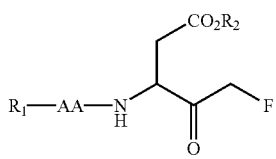

wherein $R_1$ is an N-terminal protecting group; AA is a residue of a non-natural α-amino acid, or β-amino acid; and $R_2$ is optionally substituted alkyl or H.

WO 00/61542 discloses dipeptide apoptosis inhibitors having the formula:

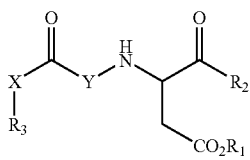

where $R_1$ is an optionally substituted alkyl or hydrogen group; $R_2$ is hydrogen or optionally substituted alkyl; Y is a residue of a natural or non-natural amino acid and $R_3$ is an alkyl, saturated carbocyclic, partially saturated carbocyclic, aryl, saturated heterocyclic, partially saturated heterocyclic or heteroaryl group, wherein said group is optionally substituted; X is O, S, $NR_4$, or $(CR_4R_5)_n$ where $R_4$ and $R_5$ are, at each occurrence, independently selected from the group consisting of hydrogen, alkyl and cycloalkyl, and n is 0, 1, 2, or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and provided that when X is O, then $R_3$ is not unsubstituted benzyl or t-butyl; and when X is $CH_2$, then $R_3$ is not H.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are particularly effective as inhibitors of caspases and cellular apoptosis. These compounds have the general formula I:

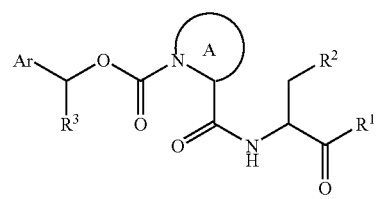

wherein:
Ring A is an optionally substituted piperidine, tetrahydroquinoline or tetrahydroisoquinoline ring;
$R^1$ is hydrogen, $CHN_2$, R, or $—CH_2Y$;
R is an optionally substituted group selected from an aliphatic group, an aryl group, an aralkyl group, a heterocyclic group, or an heterocyclylalkyl group;
Y is an electronegative leaving group;
$R^2$ is $CO_2H$, $CH_2CO_2H$, or esters, amides or isosteres thereof;
Ar is an optionally substituted aryl group; and
$R^3$ is hydrogen, an optionally substituted $C_{1-6}$ alkyl, $F_2$, CN, aryl or $R^3$ is attached to Ar to form an unsaturated or partially saturated five or six membered fused ring having 0–2 heteroatoms.

The compounds of this invention have potent inhibition properties across a range of caspase targets with good efficacy in cellular models of apoptosis. In addition, these compounds are expected to have improved cell penetration and pharmacokinetic properties and, as a consequence of their potency, have improved efficacy against diseases where caspases are implicated.

DETAILED DESCRIPTION OF THE INVENTION

This invention provides novel compounds, and pharmaceutically acceptable derivatives thereof, that are particularly effective as caspase inhibitors. The invention also provides methods for using the compounds to treat caspase-mediated disease states in mammals. The compounds have the general formula I:

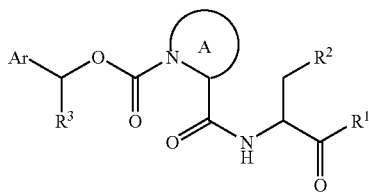

wherein:
Ring A is an optionally substituted piperidine, tetrahydroquinoline or tetrahydroisoquinoline ring;
$R^1$ is hydrogen, $CHN_2$, R, or $-CH_2Y$;
R is an optionally substituted group selected from an aliphatic group, an aryl group, an aralkyl group, a heterocyclic group, or an heterocyclylalkyl group;
Y is an electronegative leaving group;
$R^2$ is $CO_2H$, $CH_2CO_2H$, or esters, amides or isosteres thereof;
Ar is an optionally substituted aryl group; and
$R_3$ is hydrogen, an optionally substituted $C_{1-6}$ alkyl, $F_2$, CN, aryl or $R^3$ is attached to Ar to form an unsaturated or partially saturated five or six membered fused ring having 0–2 heteroatoms.

As used herein, the following definitions shall apply unless otherwise indicated. The term "aliphatic" as used herein means straight chained or branched $C_1$–$C_{12}$ hydrocarbons which are completely saturated or which contain one or more units of unsaturation. Aliphatic groups include substituted or unsubstituted linear, branched or cyclic alkyl, alkenyl, or alkynyl groups and hybrids thereof such as (cycloalkyl)alkyl, (cycloalkenyl)alkyl or (cycloalkyl)alkenyl. The term "aliphatic" includes "carbocyclic" groups. The term "alkyl" used alone or as part of a larger moiety refers to both straight and branched chains containing one to twelve carbon atoms. When the term alkyl is used as part of a larger moiety, as in aralkyl or heteroaralkyl, the alkyl portion will preferably contain one to six carbons.

The term "halogen" means F, Cl, Br, or I. The term "heteroatom" means nitrogen, oxygen or sulfur.

The term "aryl" refers to monocyclic or polycyclic aromatic groups, and monocyclic or polycyclic heteroaromatic groups containing one or more heteroatoms, having five to fourteen atoms. Such groups include, but are not restricted to phenyl, naphthyl, anthryl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, tetrahydrofuranyl, phthalimidinyl, tetrazolyl, and chromanyl.

The term "heterocyclic group" refers to saturated and unsaturated monocyclic or polycyclic ring systems containing one or more heteroatoms and a ring size of three to eight. Such groups include, but are not limited to aziranyl, oxiranyl, azetidinyl, tetrahydrofuranyl, pyrrolinyl, pyrrolidinyl, dioxolanyl, imidazolinyl, imidazolidinyl, pyrazolinyl, pyrazolidinyl, pyranyl, piperidinyl, dioxanyl, morpholinyl, dithianyl, thiomorpholinyl, piperazinyl, trithianyl, quinuclidinyl, oxepanyl, and thiepanyl.

The term "carbocyclic group" refers to saturated monocyclic or polycyclic carbon ring systems which may be fused to aryl or heterocyclic groups. Examples could include cyclohexyl, cyclopentyl, cyclobutyl, cyclopropyl, indanyl, tetrahydronaphthyl and the like.

An aliphatic, aryl, or heterocyclyl group may contain one or more substituents. Examples of suitable substituents include a halogen, —R, —OR, —OH, —SH, —SR, protected OH (such as acyloxy), phenyl (Ph), substituted Ph, —OPh, substituted —OPh, —$NO_2$, —CN, —$NH_2$, —NHR, —$N(R)_2$, —NHCOR, —NHCONHR, —$NHCON(R)_2$, —NRCOR, —$NHCO_2R$, —$CO_2R$, —$CO_2H$, —COR, —CONHR, —$CON(R)_2$, —$S(O)_2R$, —$SONH_2$, —S(O)R, —$SO_2NHR$, —$NHS(O)_2R$, =O, =S, =NNHR, =$NNR_2$, =N—OR, =NNHCOR, =$NNHCO_2R$, =$NNHSO_2R$, or =NR where R is an aliphatic group or a substituted aliphatic group.

A substitutable nitrogen on a heterocyclic ring may be optionally substituted. Suitable substituents on the nitrogen include R, COR, $S(O)_2R$, and $CO_2R$, where R is an aliphatic group or a substituted aliphatic group.

Nitrogen and sulfur may be in their oxidized form, and nitrogen may be in a quaternized form.

The term "electronegative leaving group" has the definition known to those skilled in the art (see March, *Advanced Organic Chemistry*, 4$^{th}$ Edition, John Wiley & Sons, 1992). Examples of electronegative leaving groups include halogens such as F, Cl, Br, I, aryl- and alkylsulfonyloxy groups, trifluoromethanesulfonyloxy, OR, SR, —OC=O(R), —$OPO(R^4)(R^5)$, where R is an aliphatic group, an aryl group, an aralkyl group, a carbocyclic group, an alkyl carbocyclic group, a heterocyclic group, or an alkyl heterocyclic group; and $R^4$ and $R^5$ are independently selected from R or OR.

When the $R^2$ group is in the form of an ester or amide, the present compounds undergo metabolic cleavage to the corresponding carboxylic acids, which are the active caspase inhibitors. Because they undergo metabolic cleavage, the precise nature of the ester or amide group is not critical to the working of this invention. The structure of the $R^2$ group may range from the relatively simple diethyl amide to a steroidal ester. Examples of esters of $R^2$ carboxylic acids include, but are not limited to, $C_{1-12}$ aliphatic, such as $C_{1-6}$ alkyl or $C_{3-10}$ cycloalkyl, aryl, such as phenyl, aralkyl, such as benzyl or phenethyl, heterocyclyl or heterocyclylalkyl. Examples of suitable $R^2$ heterocyclyl rings include, but are not limited to, 5–6 membered heterocyclic rings having one or two heteroatoms such as piperidinyl, piperazinyl, or morpholinyl.

Amides of $R^2$ carboxylic acids may be primary, secondary or tertiary. Suitable substituents on the amide nitrogen include, but are not limited to, one or more groups independently selected from the aliphatic, aryl, aralkyl, heterocyclyl or heterocyclylalkyl groups described above for the $R^2$ ester alcohol. Likewise, other prodrugs are included within the scope of this invention. See Bradley D. Anderson, "Prodrugs for Improved CNS Delivery" in Advanced Drug Delivery Reviews (1996), 19, 171–202.

Isosteres or bioisosteres of carboxylic acids and esters result from the exchange of an atom or group of atoms to create a new compound with similar biological properties to the parent carboxylic acid or ester. The bioisosteric replacement may be physicochemically or topologically based. An example of an isosteric replacement for a carboxylic acid is $CONHSO_2$(alkyl) such as $CONHSO_2Me$.

Compounds of this invention where $R^2$ is $CO_2H$ or $CH_2CO_2H$, γ-ketoacids or δ-ketoacids respectively, may exist in solution as either the open form (a) or the cyclized hemiketal form (b) (y=1 for γ-ketoacids, y=2 for δ-ketoacids). The representation herein of either isomeric form is meant to include the other.

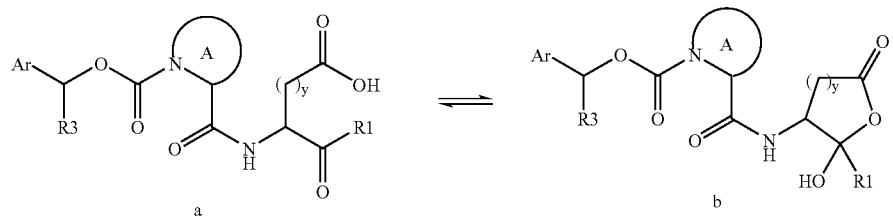

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

A number of dipeptidic ICE/caspase inhibitors that were generically and specifically described in WO 91/15557, WO 99/47154 and WO 00/61542 were tested for activity against caspases in the enzymatic and cell-based assays described below. The new compounds of formula I were found to have unexpectedly better activity relative to the previously described inhibitors.

Compounds of this invention wherein Ring A is an optionally substituted piperidine ring are represented by formula Ia below:

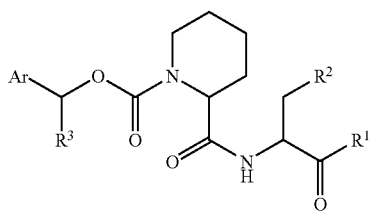

Ia

Compounds of this invention wherein Ring A is an optionally substituted tetrahydroquinoline ring are represented by formula Ib below:

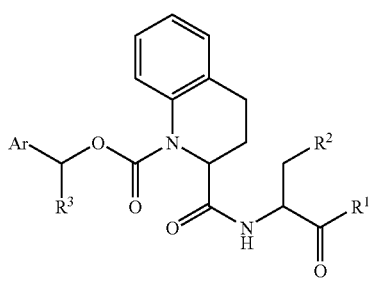

Ib

Compounds of this invention wherein Ring A is an optionally substituted tetrahydroisoquinoline ring are represented by formula Ic below:

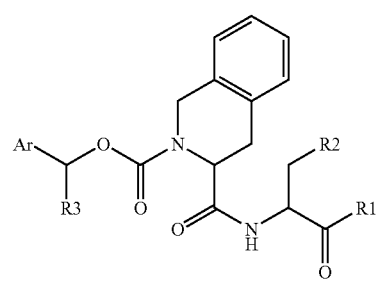

Ic

Ring A may be substituted or unsubstituted. Examples of suitable Ring A substituents include one or more groups selected from halogen, —R, —OR, —OH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is an aliphatic group or a substituted aliphatic group.

Preferred compounds of this invention are compounds of formula I that have one or more of the following features and more preferably all of the following features:

(a) R$^1$ is a halomethyl group, more preferably CH$_2$F;
(b) R$^2$ is CO$_2$H or esters, amides or isosteres thereof;
(c) R$^3$ is hydrogen, C$_{1-6}$ alkyl, or C$_{1-6}$ haloalkyl, more preferably CF$_3$ or C$_2$F$_5$; and
(d) Ar is an optionally substituted aryl, more preferably an optionally substituted phenyl.

Examples of Specific Compounds are Shown Below in Table Table 1
TABLE 1
Example 1
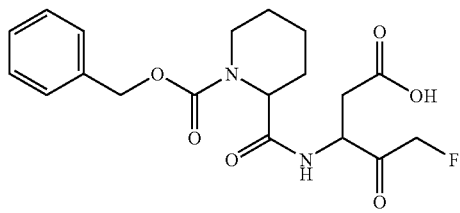
Example 2
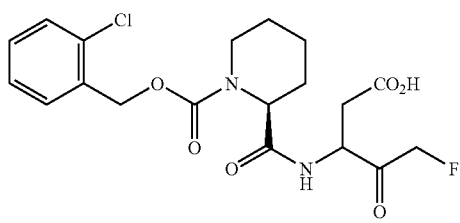
Example 3
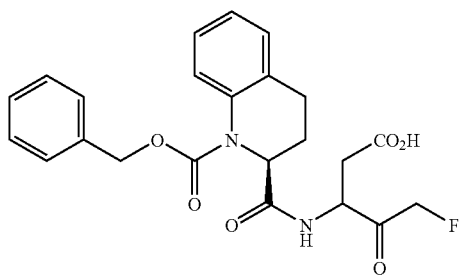
Example 4
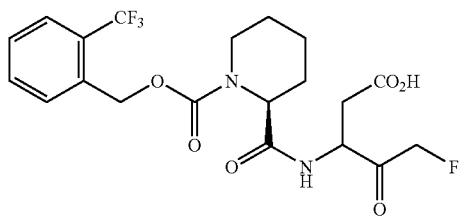
Example 5
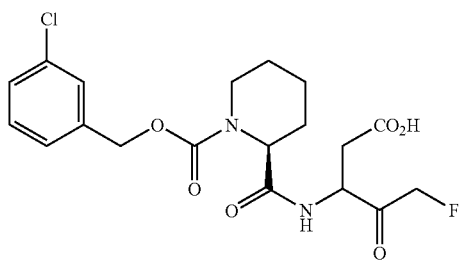

TABLE 1-continued
| | |
|---|---|
| 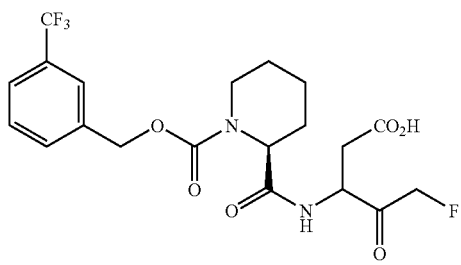 | Example 6 |
| 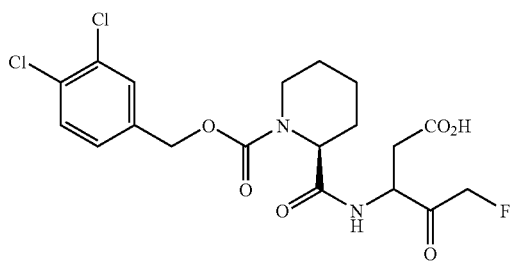 | Example 7 |
| 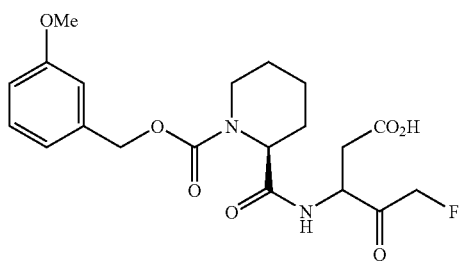 | Example 8 |
| 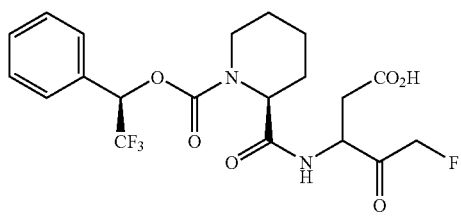 | Example 9 |
| 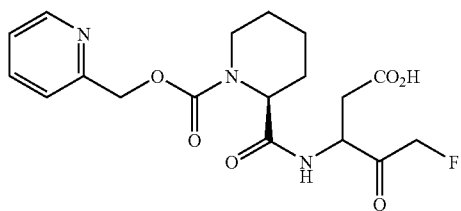 | Example 10 |
| 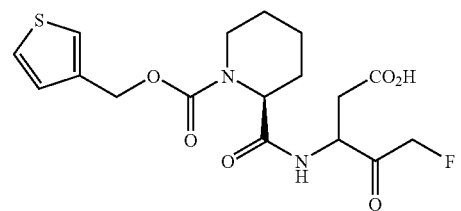 | Example 11 |

TABLE 1-continued
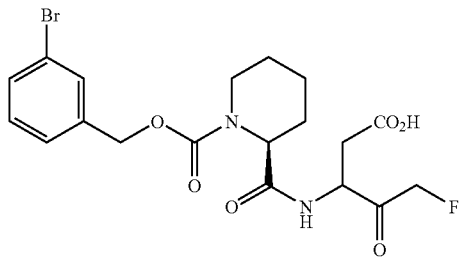
Example 12
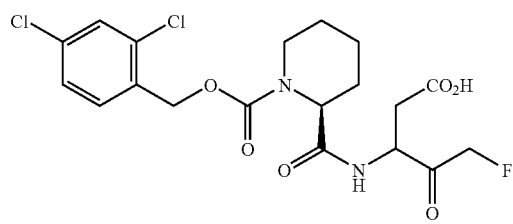
Example 13
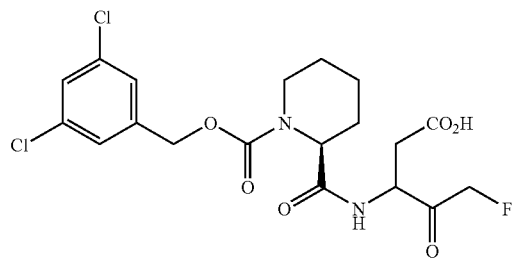
Example 14
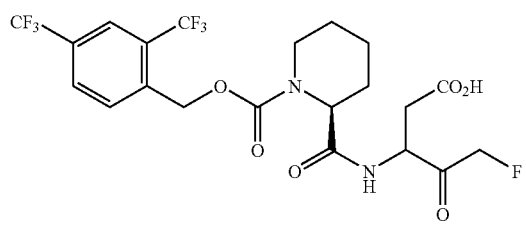
Example 15
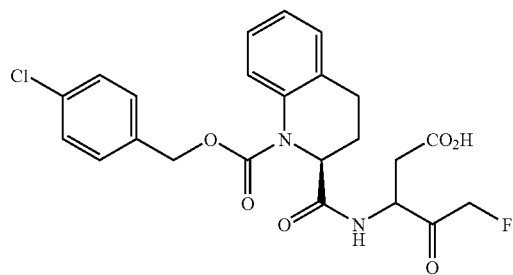
Example 16

TABLE 1-continued
| | |
|---|---|
| 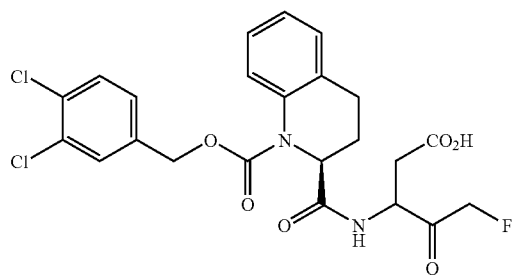 | Example 17 |
| 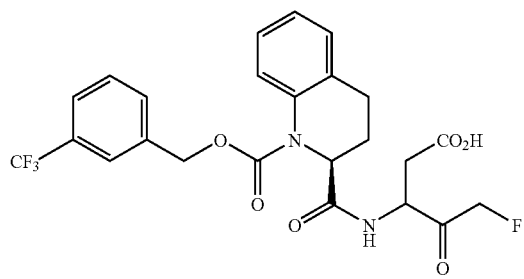 | Example 18 |
| 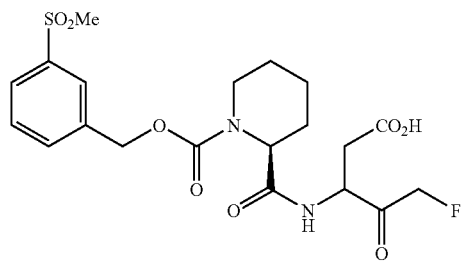 | Example 19 |
| 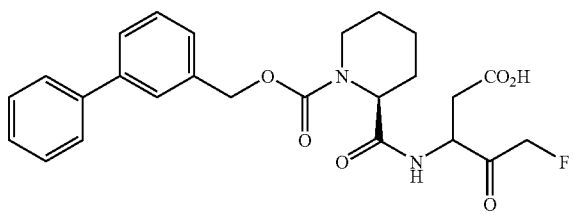 | Example 20 |
| 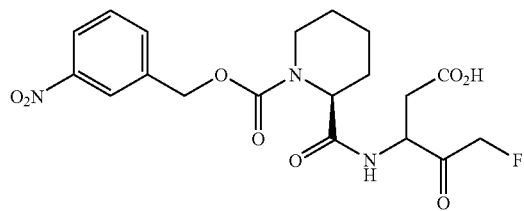 | Example 21 |
| 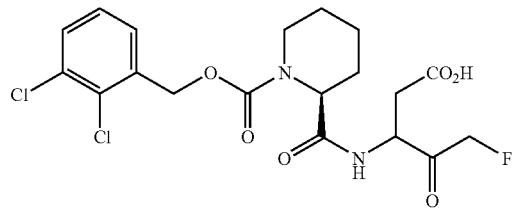 | Example 22 |

TABLE 1-continued
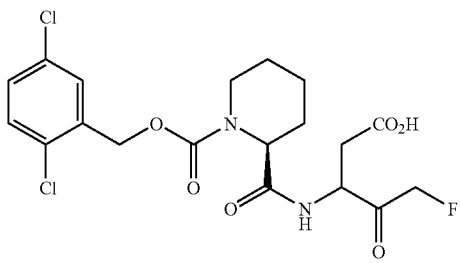
Example 23
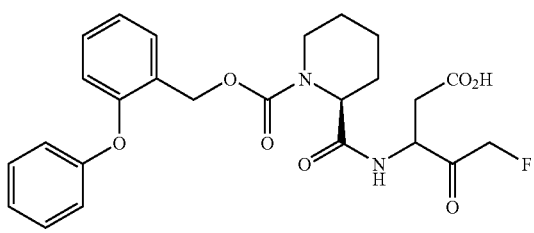
Example 24
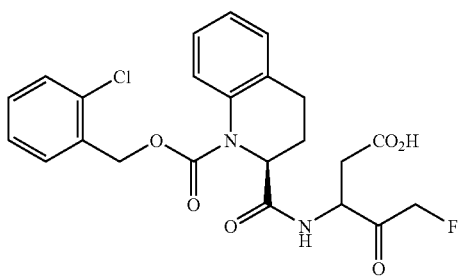
Example 25
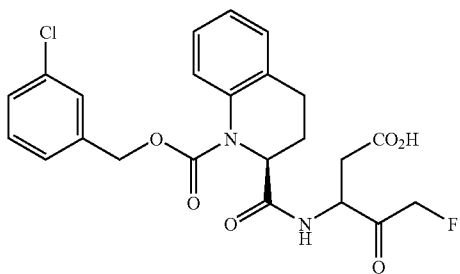
Example 26
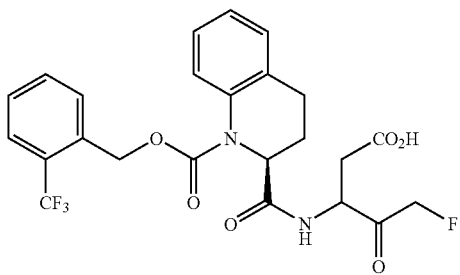
Example 27

TABLE 1-continued
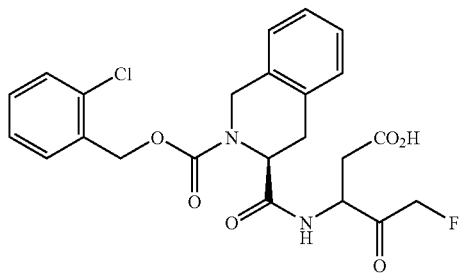
Example 28
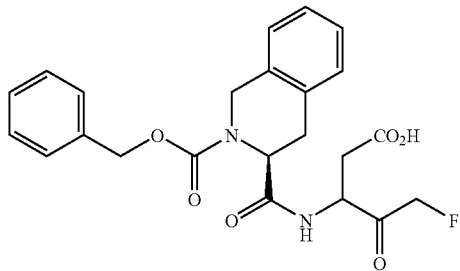
Example 29
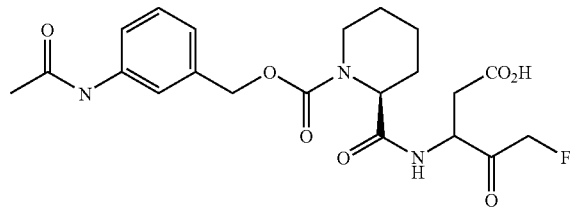
Example 30
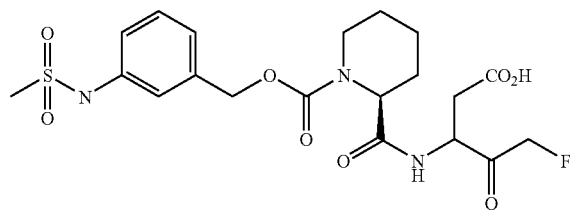
Example 31
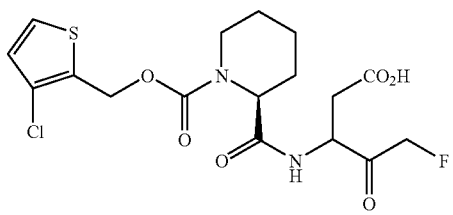
Example 32
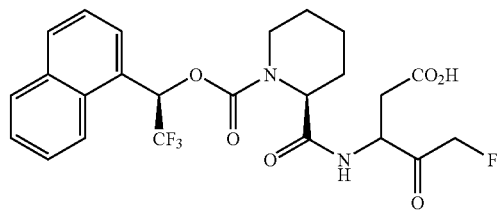
Example 33

TABLE 1-continued
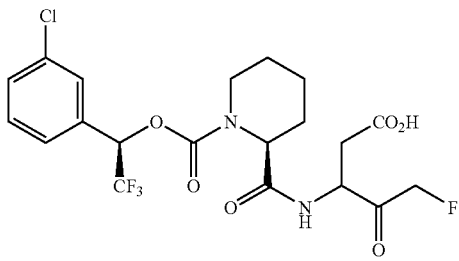
Example 34
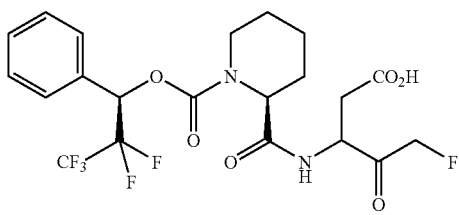
Example 35
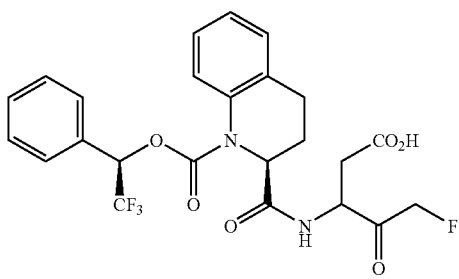
Example 36
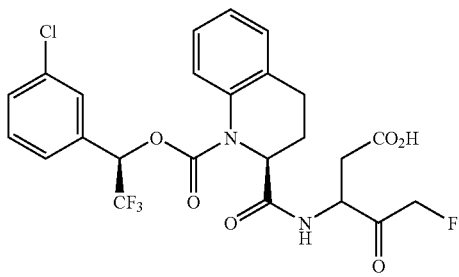
Example 37
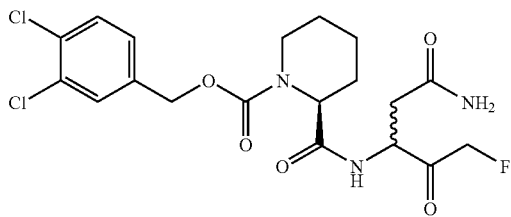
Example 38

TABLE 1-continued
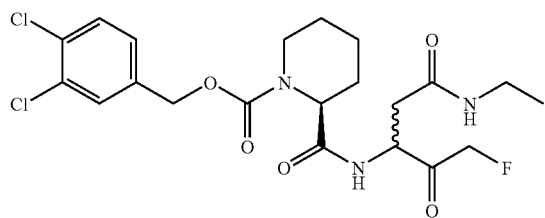
Example 39
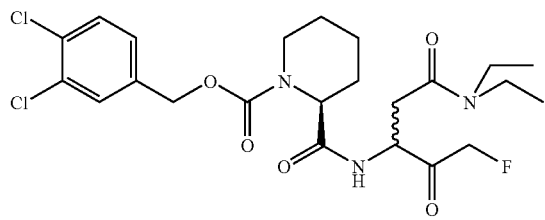
Example 40
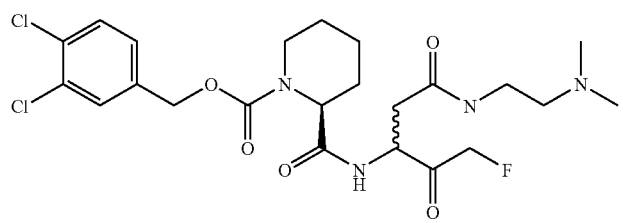
Example 41
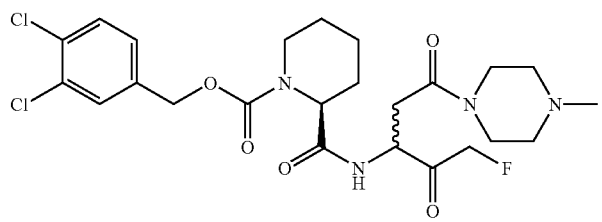
Example 42
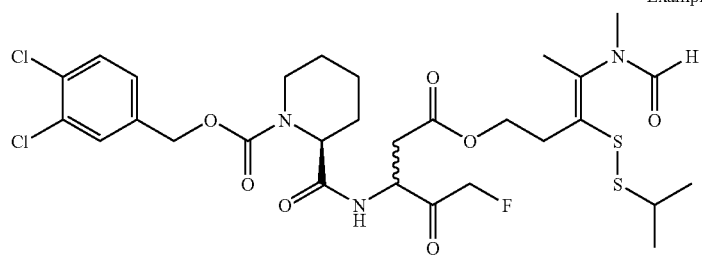
Example 43
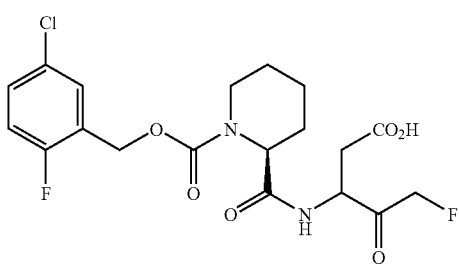
Example 44

The compounds of this invention may be prepared in general by methods known to those skilled in the art for analogous compounds, as illustrated by the general Scheme I below and by the preparative examples that follow.

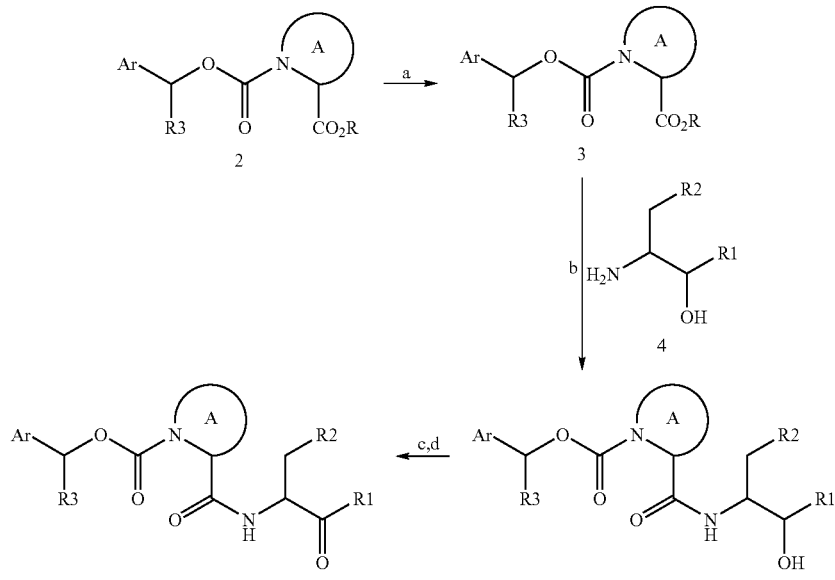

Scheme I

Details: (a) TFA or KOH/MeOH; (b) EDC/DMAP/HOBt: (c) Dess-Martin periodinane; (d) TFA/DCM In Scheme I above, the starting carbamate ester 2 (R is any suitable organic radical) is readily obtained by a carbamoylation reaction between the corresponding alcohol, ArCH(OH)—$R^3$, and the corresponding ester of piperidine-2-carboxylic acid, 1,2,3,4-tetrahydroquinoline-2-carboxylic acid or 1,2,3,4-tetrahydroisoquinoline-2-carboxylic acid. Such carbamate-forming reactions generally use phosgene or an equivalent thereof and are known to those skilled in the art (i.e. formation of an intermediate carbamoyl chloride from the amine, then reaction with the alcohol; or formation of an intermediate chloroformate from the alcohol, then reaction with the amine; or formation of an intermediate chloroformate from the alcohol, then reaction with the amine). Carbamate ester 2 is hydrolyzed using base or, when the ester is a t-butyl group, using trifluoroacetic acid. The acid 3 is then coupled with the amino alcohol 4. Depending on the nature of $R^1$ and $R^2$ an amino ketone may be used, in place of the amino alcohol, which avoids the need for a subsequent oxidation step. In the case of fluoromethyl ketones where $R^1$ is $CH_2F$, the amino alcohol 4 may be obtained according to the method of Revesz et al., *Tetrahedron Lett.*, 1994, 35, 9693. Finally the hydroxyl in compound 5 is oxidized and the compound treated appropriately according to the nature of $R^2$. For example, if the product I requires $R^2$ to be a carboxylic acid, then $R^2$ in 4 is preferably an ester and the final step in the scheme is acid or base-catalyzed deprotection.

The compounds of this invention are designed to inhibit caspases. Therefore, the compounds of this invention may be assayed for their ability to inhibit caspase activity, apoptosis, and the release of IL-1β directly. Assays for each of the activities are known in the art and are described below in detail in the Testing section.

According to another embodiment, the invention provides a composition comprising a compound of this invention or a pharmaceutically acceptable salt thereof, as described above, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylatedversions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia,epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease including alcoholic hepatitis, renal disease, polyaptic kidney disease, H. pylori-associated gastric and duodenal ulcer disease, HIV infection, tuberculosis, and meningitis. The compounds and compositions are also useful in treating complications associated with coronary artery bypass grafts and as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

Synthetic Examples

[3S/R,(2S)]-3-(1-Benzyloxycarbonyl-2-piperidinecarboxamido)-5-fluoro-4-oxo-pentanoic acid

EXAMPLE 1

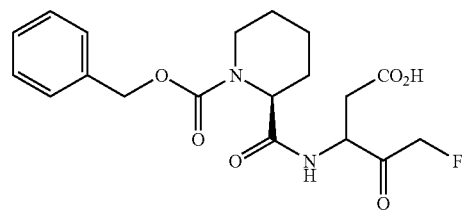

Method A:

(S)-Piperidine-1,2-dicarboxylic acid 1-benzyl ester 2-methyl ester

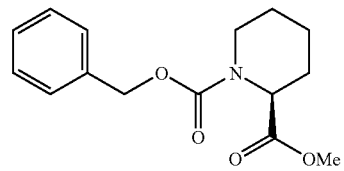

To a stirred suspension of (S)-piperidine-2-carboxylic acid methyl ester hydrochloride salt (5.0 g, 27.8 mmol) in dichloromethane (DCM) (35 mL) at 0° C. was added diisopropylethylamine (DIPEA) (10.1 mL, 58.4 mmol) followed by N-(benzyloxycarbonyloxy)succinimide (7.63 g, 30.6 mmol). The reaction mixture was allowed to warm to room temperature and stirred overnight. The residue was diluted with DCM and washed with 1.0-M HCl. The organic layer was washed with brine, dried($Na_2SO_4$), filtered and concentrated in vacuo. The residue was purified by flash chromatography (20% ethyl acetate in hexane) to afford the title compound as a pale yellow oil (7.72, 100%): $^1H$ NMR (400 MHz, $CD_3OD$) δ 1.19–1.88 (5H, m), 2.15–2.28 (1H, m), 2.91–3.12 (1H, m), 3.70–3.73 (3H, 2s), 4.00–4.07 (1H, m), 4.82–4.87 (1H, m), 5.03–5.21 (2H, m), 7.24–7.39 (5H, m); $^{13}C$ NMR (100 MHz, $CD_3OD$) δ 22.0, 22.1 ($CH_2$), 26.0, 26.1 ($CH_2$), 28.1 ($CH_2$), 43.4, 43.5 ($CH_2$), 53.1 ($CH_3$), 56.2, 56.5 (CH), 68.8, 68.9 ($CH_2$), 129.2 (CH), 129.5 (CH), 129.9 (CH), 138.4 (C), 167.0 (CO), 173.7 (CO).

Method B:

(S)-Piperidine-1,2-dicarboxylic acid 1-benzyl ester

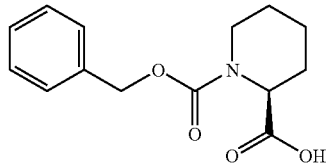

To a stirred solution of (S)-piperidine-1,2-dicarboxylic acid 1-benzyl ester 2-methyl ester (8.0g, 28.8 mmol) in MeOH (75 mL) and water (38 mL) at 0° C. was added powdered KOH (1.78 g, 31.7 mmol). The reaction mixture was allowed to stir for 16 h at room temperature and then the MeOH was removed in vacuo. The residue was diluted with water and washed DCM. The aqueous layer was acidified with 1.0-M HCl and extracted with ethyl acetate three times. The combined organic extracts were dried ($Na_2SO_4$), filtered and concentrated in vacuo to afford the title compound as pale yellow oil (7.6 g, 100%): $^1$H NMR (400 MHz, $CD_3OD$) δ 1.36–1.61 (2H, m), 1.70–1.85 (3H, m), 2.28–2.40 (1H, m), 3.05–3.26 (1H, m), 4.06–4.14 (1H, m), 4.89–5.26 (4H, m), 7.37–7.48 (5H, m); $^{13}$C NMR (100 MHz, $CD_3OD$) δ 20.5, 20.6 ($CH_2$), 24.6, 24.7 ($CH_2$), 26.6 ($CH_2$), 41.8, 41.9 ($CH_2$), 54.5, 54.7 (CH), 67.2, 67.3 ($CH_2$), 127.6 (CH), 127.9 (CH), 128.4 (CH), 136.9 (C), 173.4 (CO).

Method C:

[3S/R,(2S)]-3-(1-Benzyloxycarbonyl-2-piperidinecarboxamido)-5-fluoro-4-hydroxy-pentanoic acid tert-burtyl ester

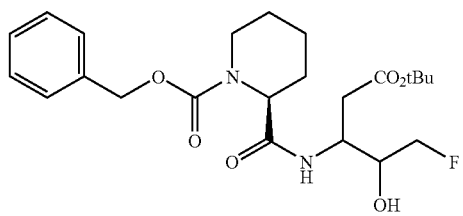

A stirred mixture of (S)-piperidine-1,2-dicarboxylic acid 1-benzyl ester (606 mg, 2.30 mmol), 3-amino-5-fluoro-4-hydroxy-pentanoic acid tert-butyl ester (500 mg, 2.42 mmol), HOBT (344 mg, 2.53 mmol), DMAP (323 mg, 2.65 mmol) and anhydrous THF (17 mL) was cooled to 0° C. then EDC (485 mg, 2.53 mmol) was added. The mixture was allowed to warm to room temperature during 16 h then concentrated under reduced pressure. The residue purified by flash chromatography (5% ethyl acetate in petroleum spirit –50% ethyl acetate in petroleum spirit) to give the title compound as a colorless oil (871 mg, 84%): $^1$H NMR (400 MHz, $CDCl_3$) δ 1.44 (9H, s), 1.50–3.09 (9H, m), 3.87–5.18 (9H, m), 6.72–7.04 (1H, m), 7.22–7.37 (5H, m); $^{19}$F NMR (376 MHz, $CDCl_3$) δ −229.1, −229.3, −230.0, −230.3, −230.5.

Method D:

[3S/R,(2S)]-3-(1-Benzyloxycarbonyl-2-piperidinecarboxamido)-5-fluoro-4-oxo-pentanoic acid tert-butyl ester

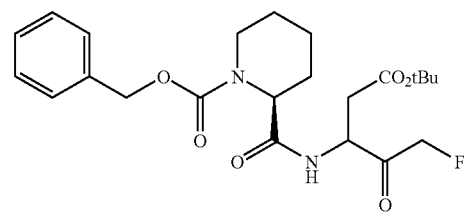

A stirred solution of [3S/R,(2S)]-3-(1-benzyloxycarbonyl-2-piperidinecarboxamido)-5-fluoro-4-hydroxy-pentanoic acid tert-butyl ester (871 mg, 1.93 mmol) in anhydrous dichloromethane (DCM) (40 mL) was treated at 0° C. with 1,1,1 triacetoxy-1,1-dihydro-1,2-beziodoxol-3(1H)-one (980 mg, 2.31 mmol). The mixture was stirred at room temperature for 16 h, diluted with ethyl acetate and washed with a 1:1 mixture of aqueous $NaHSO_4$ and aqueous $Na_2S_2O_3$. The organic layer was collected, dried ($MgSO_4$) and concentrated. The residue was purified by flash chromatography (40% ethyl acetate in hexane) to give the title compound as a colorless oil (738 mg, 85%): $^1$H NMR (400 MHz, $CDCl_3$) δ 1.46 (9H, s), 1.39–1.74 (5H, m), 2.25–2.36 (1H, m), 2.70–3.06 (3H, m), 4.09–4.12 (1H, m), 4.80–5.19 (6H, m), 7.01–7.15 (1H, m), 7.28–7.37 (5H, m); $^{13}$C NMR (100 MHz, $CDCl_3$) δ 20.7 ($CH_2$), 25.1/26.0 ($CH_2$), 28.3 ($CH_3$), 36.6, 36.7 ($CH_2$), 42.5, 42.7 ($CH_2$), 52.8 (CH), 55.2 (CH), 68.1, ,68.2 ($CH_2$), 82.7 (C), 84.5, 84.6 ($CH_2F$), 128.3 (CH), 128.6 (CH), 129.0 (CH), 136.7 (C), 170.3, 170.4 (CO), 171.5 (CO), 202.0 (CO); $^{19}$F NMR (376 MHz, $CDCl_3$) δ −231.6, −231.9, −232.2.

Method E:

[3S/R,(2S)]-3-(1-Benzyloxycarbonyl-2-piperidinecarboxamido)-5-fluoro-4-oxo-pentanoic acid

EXAMPLE 1

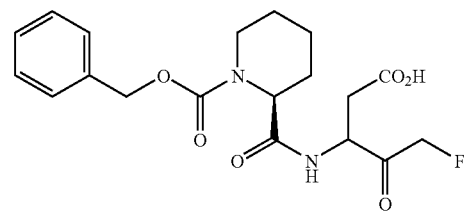

Trifluoroacetic acid (TFA) (12 mL) was added to a stirred ice cold solution of [3S/R,(2S)]-3-(1-benzyloxycarbonyl-2-piperidinecarboxamido)-5-fluoro-4-oxo-pentanoic acid tert-butyl ester (698 mg, 1.55 mmol) in anhydrous DCM (38 mL). The mixture was stirred at 0° C. for 0.5 h then at room temperature for 0.5 h. The mixture was concentrated under reduced pressure and then the residue was dissolved in dry DCM. This process was repeated several times in order to remove excess TFA. The gum was lyophilized twice from HPLC grade water/acetonitrile to afford the title compound as a white solid foam (481 mg, 79%): IR (solid) 1736, 1665, 1517, 1436, 1255, 1174, 1041, 931 cm$^{-1}$; $^1$H NMR (400 MHz, d$_6$-DMSO) δ 1.12–1.40 (2H, m), 1.45–1.68 (3H, m), 2.05 (1H, m), 2.61–2.63 (1H, m), 2.70–2.87 (1H, m), 2.98–3.21 (1H, m), 3.91 (1H, m), 4.28–4.75 (3H, m), 4.91–5.30 (3H, m), 7.25–7.42 (5H, m), 7.80–8.59 (1H, brm), 12.5 (1H, brs); $^{13}$C NMR (100 MHz, d$_6$-DMSO) δ (DMSO) 20.0 (CH$_2$), 24.6 (CH$_2$), 27.3 (CH$_2$), 34.7 (CH$_2$), 42.1 (CH$_2$), 52.1, 52.4 (CH), 54.5 (CH), 66.7 (CH$_2$), 84.2 (CH$_2$F), 127.8 (ArCH), 128.1 (ArCH), 128.7 (ArCH), 131.1 (ArC), 171.4 (CO), 172.0 (CO), 172.1 (CO), 202.8 (CO); $^{19}$F NMR (376 MHz, d$_6$-DMSO) δ –226.6, –226.8, –226.9, –232.4, –232.6, –232.7; MS (FAB +ve, HR) Calculated for C$_{19}$H$_{24}$FN$_2$O$_6$ (MH+) 395.1618, found 395.1625.

[3S/R,(2S)]-3-(1-(2-Chlorobenzyloxycarbonyl)-2-piperidinecarboxamido)-5-fluoro-4-oxo-pentanoic acid

EXAMPLE 2

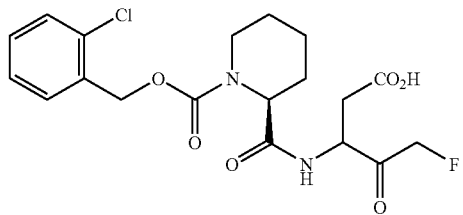

Method F:

(S)-1-(2-Chlorobenzyloxycarbonyl)-piperidine-2-carboxylic acid methyl ester

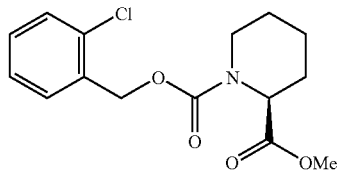

To a vigorously stirred solution of (S)-pipecolic acid methyl ester hydrochloride (500 mg, 2.79 mmol) in dry DCM (10 mL) cooled in an ice-bath, was added dropwise Et$_3$N (705 mg, 6.96 mmol) followed by 2-chlorobenzyl chloroformate (made from 2-chlorobenzyl alcohol using the method described in *J. Med. Chem.*, 1998, 41, 1315–1343) (857 mg, 4.18 mmol). The resulting suspension was stirred at 0° C. for a further 0.75 h, diluted with ethyl acetate (30 mL) and poured into 1.0-M HCl (30 mL). The organic layer was separated and washed sequentially with 1.0-M HCl (20 mL), aq.NaHCO$_3$ (20 mL) and brine (20 mL). The organic layer was then dried (NaSO$_4$), filtered and concentrated under reduced pressure to give a colorless oil. The oil was purified by column chromatography (15% ethyl acetate in hexane) to give the title compound as a colorless viscous oil (824 mg, 95%): $^1$H NMR (400 MHz, CDCl$_3$) 1.2–1.4 (1H, m), 1.4–1.6 (1H, m), 1.6–1.8 (3H, m), 2.2–2.3 (1H, m), 2.9–3.2 (1H, m), 3.7–3.8 (3H, m), 4.0–4.2 (1H, m), 4.8–5.0 (1H, m), 5.2–5.4 (2H, m), 7.2–7.3 (2H, m), 7.3–7.5 (2H, m)

[3S/R,(2S)]-3-(1-(2-Chlorobenzyloxycarbonyl)-2-piperidinecarboxamido)-5-fluoro-4-oxo-pentanoic acid

EXAMPLE 2

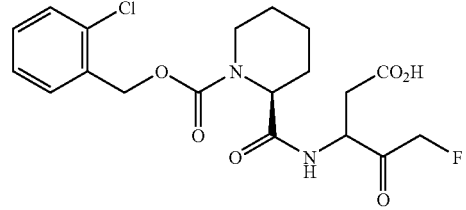

This was prepared from (S)-1-(2-chlorobenzyloxycarbonyl)-piperidine-2-carboxylic acid methyl ester using procedures similar to those described above in Methods B–E (161 mg, 70% last step): IR (solid) 1668, 1789 cm$^{-1}$; $^1$H NMR (400 MHz, d$_6$-DMSO) δ 1.1–1.8 (5H, m), 2.0–2.2 (1H, m), 2.4–2.9 (2H, m), 3.0–3.5 (1H, m), 3.8–4.0 (1H, m), 4.2–4.8 (3H, m), 5.0–5.4 (3H, m), 7.3–7.6 (4H, m), 7.8–8.7 (1H, m), 12.0–13.0 (1H, br s); $^{13}$C NMR (100 MHz, d$_6$-DMSO) δ 20.50, 20.77, 25.01, 25.14, 27.80, 28.18 (CH$_2$), 33.40, 35.20 (CH$_2$), 42.71 (CH$_2$), 47.89, 48.05, 52.65, 52.91, 53.35, 54.82, 55.05 (2×CH), 64.66, 64.77 (CH$_2$), 81.94, 82.04, 83.70, 83.80, 85.60 (CH$_2$), 128.21, 130.11, 130.18, 130.40, 130.61 (ArCH), 133.08, 134.93, 134.95 (ArC), 155.72, 156.40, 171.72, 172.20, 172.39, 172.58, 172.65, 173.83, 203.14, 203.29 (CO); $^{19}$F NMR (376 MHz, d$_6$-DMSO) δ –226.6, –226.8, –226.9, –230.2, –230.4, –232.4, –232.6, –232.6; Low Res MS ES+ 429.4, ES– 427.5.

[3S/R,(2S)]-3-(1-Benzyloxycarbonyl-1,2,3,4-tetrahydro-quinolinyl-2-carboxamido)-5-fluoro-4-oxo-pentanoic acid

EXAMPLE 3

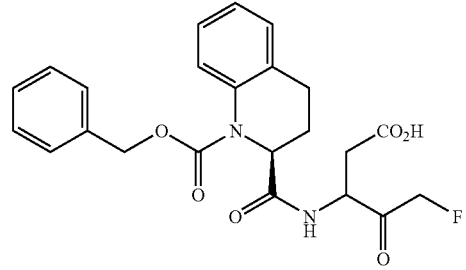

This was prepared from (S)-1-benzyloxycarbonyl-1,2,3,4-tetrahydro-quinoline-2-carboxylic acid (U.S. Pat. No. 4,461,896) using procedures similar to those described above in Methods C–E (142 mg, 100%): IR (solid) 2981, 1684, 1653, 1522, 1492, 1394, 1323, 1207, 1053, 1018; $^1$H NMR (400 MHz, d$_6$-DMSO) □ 1.71 (1H, m), 2.29 (1H, m), 2.31–2.88 (4H, m), 4.00–5.30 (6H, m), 6.97 (1H, m), 7.12 (2H, m), 7.38 (5H, m), 7.69 (1H, m), 8.25+8.62+8.72 (1H, 3×m); $^{13}$C NMR (100 MHz, d$_6$-DMSO) δ 26.07, 26.20 (CH$_2$), 28.52, 28.76, 28.95 (CH$_2$), 35.13, 35.34 (CH$_2$), 52.54, 53.21 (CH), 58.31, 58.35 (CH), 84.73 (FCH$_2$, J 177 Hz), 124.34, 126.96, 128.27, 128.39, 128.45, 128.49, 128.55, 128.78, 128.83 (CH), 132.19, 12.41 (C), 137.04, 137.78 (C=O), 154.98 (C=O), 172.66, 172.73 (C=O), 203.00, 203.15, 203.29 (FCH$_2$C=O); $^{19}$F NMR (376 MHz, d$_6$-DMSO) δ −226.59 (t, J 45 Hz), −226.91 (t, J 45 Hz), −232.76 (t, J 45 Hz).

[3S/R,(2S)]-5-Fluoro-4-oxo-3-(1-(2-trifluoromethyl-benzyloxycarbonyl)-2-piperidinecarboxamido)-pentanoic acid

EXAMPLE 4

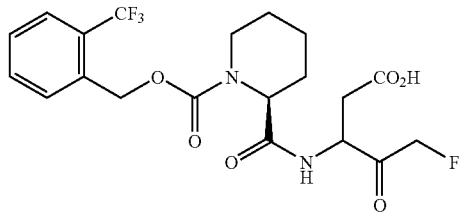

This was prepared from 2-trifluoromethylbenzyl alcohol using procedures similar to those described above in Methods F, and B–E to give an off-white solid (150 mg, 79% last step): IR (solid) 1672, 1737, 17867 cm$^{-1}$; $^1$H NMR (400 MHz, d$_6$-DMSO) δ1.1–1.4 (2H, m), 1.5–1.7 (3H, m), 2.0–2.2 (1H, m), 2.5–2.6 (1H, m), 2.7–3.0 (1H, m), 3.0–3.4 (1H, m), 3.9–4.0 (1H, m), 4.3–4.8 (2.7H, m), 5.0–5.4 (3.3H, m), 7.5–7.9 (4H, m), 7.9–8.6 (1H, m); $^{13}$C NMR (100 MHz, d$_6$-DMSO) δ 19.98, 20.23, 24.50, 27.27, 27.62 (CH$_2$), 32.96, 34.65 (CH$_2$), 42.12 (CH$_2$), 47.45, 47.60, 52.15, 52.41, 52.89, 54.52 (2×CH), 63.11, 63.38 (CH$_2$), 81.48, 81.57, 83.32, 85.05(CH$_2$F), 120.53, 123.35, 125.97 (ArC), 126.35, 128.94, 130.13, 133.18 (ArCH), 135.07 (ArC), 171.56, 172.02, 172.07, 173.26, 174.14, 202.70 (CO); $^{19}$F NMR (376 MHz, d$_6$-DMSO) δ −59.3, −226.7, −226.7, −226.8, −226.9, −230.2, −230.5, −232.5, −232.6, −232.7, −232.7.

[3S/R,(2S)]-3-(1-(3-Chlorobenzyloxycarbonyl)-2-piperidinecarboxamido)-5-fluoro-4-oxo-pentanoic acid

EXAMPLE 5

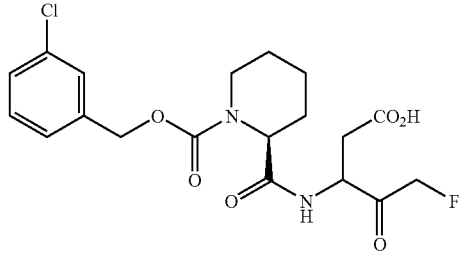

This was prepared from 3-chlorobenzyl alcohol using procedures similar to those described above in Methods F, and B–E to give an off-white solid (99 mg, 54% last step): IR (solid) 1672, 1788 cm$^{-1}$; $^1$H NMR (400 MHz, d$_6$-DMSO) δ 1.1–1.4 (2H, m), 1.5–1.7 (3H, m), 2.0–2.2 (1H, m), 2.4–2.6 (1H, m), 2.6–2.9 (1H, m), 3.0–3.3 (1H, m), 3.8–4.0 (1H, m), 4.2–4.8 (2.7H, m), 5.0–5.3 (3.3H, m), 7.2–7.5 (4H, m), 7.5–8.7 (1H, m); $^{13}$C NMR (100 MHz, d$_6$-DMSO) δ 19.99, 20.24, 24.57, 27.09, 27.27, 27.63 (CH$_2$), 32.96, 34.72, 34.86 (CH$_2$), 42.14 (CH$_2$), 47.45, 47.61, 52.20, 52.40, 52.87, 54.53 (2×CH), 65.79 (CH$_2$), 81.51, 81.56, 83.28, 85.06 (CH$_2$F), 126.99, 127.50, 128.05, 130.65 (ArCH), 133.40, 139.72, 139.75 (ArC), 171.26, 171.80, 172.03, 172.08, 173.27, 174.14, 202.58, 202.72 (CO); $^{19}$F NMR (376 MHz, d$_6$-DMSO) δ −226.6, −226.8, −226.9, −230.2, −230.3, −232.4, −232.5, −232.6.

[3S/R,(2S)]-5-Fluoro-4-oxo-3-(1-(3-trifluoromethyl-benzyloxycarbonyl)-2-piperidinecarboxamido)-pentanoic acid

EXAMPLE 6

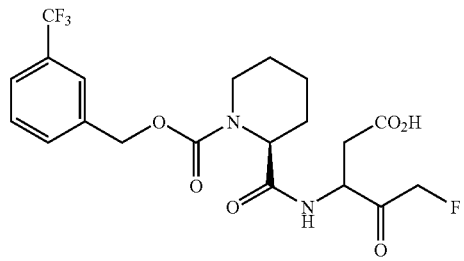

This was prepared from 3-trifluoromethylbenzyl alcohol using procedures similar to those described above in Methods F, and B–E to give an off-white solid (142 mg, 64% last step): IR (solid) 1670, 1788 cm$^{-1}$; $^1$H NMR (400 MHz, d$_6$-DMSO) δ 1.1–1.7 (5H, m), 2.0–2.2 (1H, m), 2.5–2.9 (2H, m), 3.0–3.3 (1H, m), 3.8–4.0 (1H, m), 4.2–4.8 (3H, m), 4.9–5.3 (3H, m), 7.5–7.8 (4H, m), 7.8–8.6 (1H, m); $^{13}$C NMR (100 MHz, d$_6$-DMSO) δ 20.02, 20.28, 24.63, 27.10, 27.28, 27.66 (CH$_2$), 32.86, 34.69 (CH$_2$), 42.19 (CH$_2$), 47.40, 47.57, 52.19, 52.40, 54.58 (2×CH), 65.29, 65.89 (CH$_2$Ar), 83.30, 85.02 (CH$_2$F), 124.20, 124.89, 129.91, 131.80 (4×ArCH), 138.71, 138.74 (2×ArC), 171.91, 172.09, 172.13, 173.33 (CO); $^{19}$F NMR (376 MHz, d$_6$-DMSO) δ −61.5, −226.7, −226.9, −226.9, −230.2, −230.4, −232.5, −232.6, −232.7; Low Res MS ES+ 461.3, ES− 463.2.

[3S/R,(2S)]-3-(1-(3,4-Dichlorobenzyloxycarbonyl)-2-piperidinecarboxamido)-5-fluoro-4-oxo-pentanoic acid

EXAMPLE 7

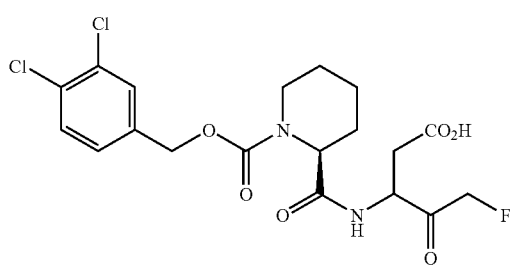

This was prepared from 3,4-dichlorobenzyl alcohol using procedures similar to those described above in Methods F, and B–E to give an off-white solid (167 mg, 70% last step): IR (solid) 1671, 1785 cm$^{-1}$; $^1$H NMR (400 MHz, d$_6$-DMSO) δ 1.1–1.8 (5H, m), 2.0–2.2 (1H, m), 2.5–2.9 (2H, m), 3.0–3.3 (1H, m), 3.8–4.0 (1H, m), 4.2–4.8 (2.5H, m), 5.0–5.4 (3.5H, m), 7.2–7.4 (1H, m), 7.5–7.7 (2H, m), 7.7–8.6 (1H, m); $^{13}$C NMR (100 MHz, d$_6$-DMSO) δ 19.99, 24.45, 24.61, 27.26, 27.61 (3×CH$_2$), 32.88, 34.68 (CH$_2$), 42.71 (CH$_2$), 47.42, 47.57, 52.20, 52.40, 54.52 (2×CH), 65.12, 65.27 (CH$_2$Ar), 81.53, 83.30, 85.08 (CH$_2$F), 127.87, 128.03, 129.59, 129.76 (ArCH), 130.64 (ArC), 131.01 (ArCH), 131.37, 138.39, 138.42 (ArC), 171.88, 172.07, 172.12, 173.32, 202.78 (CO); $^{19}$F NMR (376 MHz, d$_6$-DMSO) δ −226.6, −226.8, −226.9, −230.2, −230.3, −232.4, −232.6, −232.6.

[3S/R,(2S)]-5-Fluoro-3-(1-(3-methoxybenzyloxycarbonyl)-2-piperidinecarboxamido)-4-oxo-pentanoic acid

EXAMPLE 8

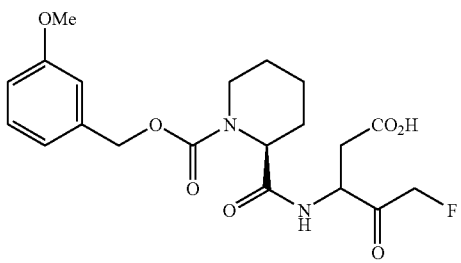

This was prepared from 3-methoxybenzyl alcohol using procedures similar to those described above in Methods F, and B–E to give an off-white solid (112 mg, 58% last step): IR (solid) 1670, 1738, 1785 cm$^{-1}$; $^1$H NMR (400 MHz, d$_6$-DMSO) δ 1.1–1.7 (5H, m), 2.0–2.2 (1H, m), 2.5–3.0 (2H, m), 3.0–3.3 (1H, m), 3.8 (3H, s), 3.8–4.0 (1H, m), 4.3–4.8 (2.5H, m), 5.0–5.4 (3.5H, m), 6.8–7.0 (3H, m), 7.2–7.3 (1H, m), 7.7–8.6 (1H, m); $^{13}$C NMR (100 MHz, d$_6$-DMSO) δ 20.01, 20.29, 24.51, 24.64, 27.31 (3×CH$_2$), 32.89, 34.64, 34.71 (CH$_2$), 42.14 (CH$_2$), 47.40, 52.17, 52.37, 54.50 (2×CH), 55.36 (OCH$_3$), 66.51 (CH$_2$Ar), 81.42, 81.52, 83.28, 85.09 (CH$_2$F), 113.15, 113.51, 119.61, 119.74, 129.88 (ArCH), 138.71, 138.78, 156.71, 159.62 (ArC), 171.96, 172.08, 172.14, 173.33, 202.65, 202.80 (CO); $^{19}$F NMR (376 MHz, d$_6$-DMSO) δ −226.7, −226.8, −226.9, −230.2, −230.4, −230.4, −232.4, −232.6, −232.6.

[3S/R,(2S, α-R)]-5-Fluoro-3-(1-(□-trifluoromethylbenzyloxycarbonyl)-2-piperidinecarboxamido)-4-oxo-pentanoic acid

EXAMPLE 9

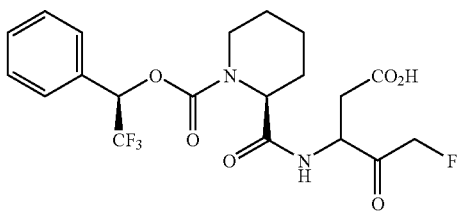

This was prepared from (R)-(−)-α-(trifluoromethyl)-benzyl alcohol using procedures similar to those described above in Methods F, and B–E to give an off-white solid (11 mg, 54% last step): $^1$H NMR (400 MHz, d$_6$-DMSO) δ 1.1–1.8 (5H, m), 1.9–2.2 (1H, m), 2.3–3.0 (2H, m), 3.0–3.5 (1H, m), 3.8–4.2 (1H, m), 4.3–4.9 (2.5H, m), 5.0–5.3 (1.5H, m), 6.2–6.4 (1H, m), 7.4–7.6 (5H, m), 7.8–8.7 (1H, m); $^{19}$F NMR (376 MHz, d$_6$-DMSO) δ −75.7, −232.1, −232.5, −232.6, −232.7.

[3S/R,(2S)]-5-Fluoro-4-oxo-3-(1-(2-pyridinylmethoxycarbonyl)-2-piperidinecarboxamido)-pentanoic acid

EXAMPLE 10

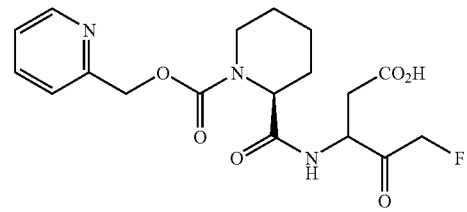

Method G:

(S)-1-(2-Pyridinylmethoxycarbonyl)-piperidine-2-carboxylic acid methyl ester

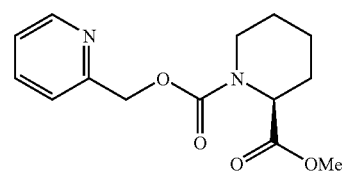

To a solution of 2-pyridylcarbinol (209 □L, 2.17 mmol) and dry THF (10 mL) at 0° C. under an atmosphere of nitrogen was added NaH (60% dispersion in mineral oil, 87 mg, 2.17 mmol), and the reaction mixture was stirred at 0° C. for 30 mins. This mixture was then added dropwise to a solution of (S)-1-(chlorocarbonyl)-2-piperidinecarboxylic acid methyl ester (EP 75737) (425 mg, 2.06 mmol) and dry THF (10 mL) at 0° C. The reaction mixture was allowed to stir for 1.5 h while warming to room temperature, then poured onto aq.KHSO$_3$ (25 mL) and extracted with EtOAc (2×50 mL). The combined organic phases were washed with aq.NaHCO$_3$, followed by brine, dried (MgSO$_4$), filtered and concentrated in vacuo. The residue was purified by column chromatography (30% ethyl acetate in hexane) to give the title compound as a colorless oil (340 mg, 59%): $^1$H NMR (400 MHz, CDCl$_3$) δ 1.3–1.8 (5H, m), 2.3 (1H, bs), 3.0 (0.5H, t, J 12.0 Hz), 3.1 (0.5H, t, J 12.0 Hz), 3.9 (3H, s), 4.2 (1H, m), 5.0 (1H, m), 5.3 (2H, dd, J 14.0 Hz), 7.2–7.4 (2H, m), 7.7 (1H, m), 8.6 (1H, m)

[3S/R,(2S)]-5-Fluoro-4-oxo-3-(1-(2- pyridinylmethoxycarbonyl)-2-piperidinecarboxamido)-pentanoic acid

EXAMPLE 10

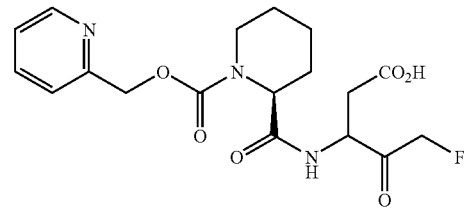

This was prepared from (S)-1-(2-pyridinylmethoxycarbonyl)-piperidine-2-carboxylic acid methyl ester using procedures similar to those described above in Methods B–E to give a clear glass (67 mg, 100% last step): $^1$H NMR (400 MHz, $d_6$-DMSO) δ 1.23–1.61 (5H, m), 2.59 (1H, m), 2.82 (1H, m), 3.21 (1H, m), 3.95 (1H, m), 4.29–4.75 (3H, m), 5.09–5.21 (4H, m), 7.45–7.52 (2H, m), 7.94–8.59 (3H, m), 12.5 (1H, bs); $^{13}$C NMR (100 MHz, $d_6$-DMSO) δ 18.48 ($CH_2$), 22.97 ($CH_2$), 23.13 ($CH_2$), 25.73 ($CH_2$), 33.15 ($CH_2$), 40.74 ($CH_2$), 50.67, 50.94 (CH), 53.08 (CH), 64.85, 65.10 ($CH_2$), 81.85 (d, J 178 Hz, $CH_2F$), 120.63 (CH), 122.27 (CH), 137.55 (CH), 146.61 (CH), 154.34 (C), 156.92, 157.28 (C), 170.56, 170.63 (C), 171.81 (C), 201.25 (CO); $^{19}$F NMR (376 MHz, $d_6$-DMSO) δ −75.21, −226.66, −226.70, −226.83, −226.87, −230.37, −232.38, −232.57, −232.62, −232.64.

[3S/R,(2S) ]-5-Fluoro-4-oxo-3-(1-(3-thienyl-methoxycarbonyl)-2-piperidinecarboxamido)-pentanoic acid

EXAMPLE 11

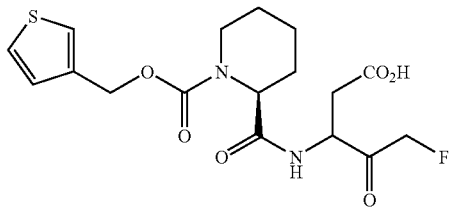

This was prepared from 3-thiophenemethanol using procedures similar to those described above in Methods G, and B–E to give a white solid (27 mg, 39% last step) after preparative HPLC: IR (solid) 3339, 2952, 1786, 1735, 1663 cm$^{-1}$; $^1$H NMR (400 MHz, $d_6$-DMSO) δ 1.22–1.32 (2H, m), 1.41–1.57 (3H, m), 2.67 (1H, m), 2.71 (1H, m), 3.08 (1H, m), 3.87 (1H, m), 4.64–5.53 (5H, m), 7.08 (1H, m), 7.45–7.52 (2H, m), 8.44 (1H, m), 12.50 (1H, bs); $^{13}$C NMR (100 MHz, $d_6$-DMSO) δ 18.48, 18.58 ($CH_2$), 23.11 ($CH_2$), 25.87 ($CH_2$), 38.98 ($CH_2$), 52.71 (CH), 52.94 (CH), 60.87, 60.90 ($CH_2$), 122.22 (CH), 122.73 (CH), 126.07, 126.32 (CH), 136.50 (C), 170.23 (CO); No signal seen for AspCH$_2$, CH$_2$F or ketone CO, due to broadening of the signals; $^{19}$F NMR (376 MHz, $d_6$-DMSO) δ −226.62, −226.85, −226.90, −230.28, −232.37, −232.58, −232.69.

[3S/R,(2S)]-3-(1-(3-Bromobenzyloxycarbonyl)-2-piperidinecarboxamido)-5-fluoro-4-oxo-pentanoic acid

EXAMPLE 12

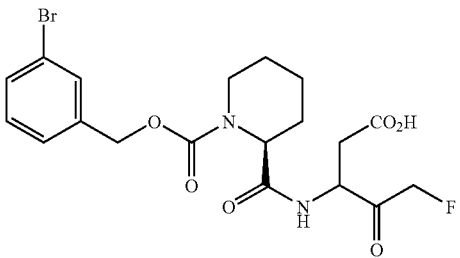

This was prepared from 3-bromobenzyl alcohol using procedures similar to those described above in Methods G, and B–E to give a white solid (119 mg, 58% last step): IR (solid) 1670, 1738, 1785 cm$^{-1}$; $^1$H NMR (400 MHz, $d_6$-DMSO) δ1.1–1.7 (5H, m), 2.0–2.2 (1H, m), 2.4–2.9 (2H, m), 2.9–3.3 (1H, m), 3.8–4.0 (1H, m), 4.2–4.8 (2.6H, m), 5.0–5.4 (3.4H, m), 7.2–7.4 (2H, m), 7.4–7.6 (2H, m), 7.7–8.7 (1H, m); $^{13}$C NMR (100 MHz, $d_6$-DMSO) δ 19.98, 20.26, 24.61, 27.09, 27.29, 27.66 ($CH_2$), 32.90, 34.71 ($CH_2$), 42.17 ($CH_2$), 47.40, 47.57, 52.19, 52.38, 54.32, 54.52 (2×CH), 65.80 ($CH_2Ar$), 81.54, 83.30, 85.10 ($CH_2F$), 121.96 (ArC), 126.54, 126.76, 130.28, 130.44, 130.98 (ArCH), 139.97, 140.00 (ArC), 156.05, 171.75, 172.08, 173.32, 202.78 (CO); $^{19}$F NMR (376 MHz, $d_6$-DMSO) δ −226.6, −226.8, −226.9, −230.1, −230.2, −230.3, −232.4, −232.5, −232.5, −232.6.

[3S/R,(2S)]-3-(1-(2,4-Dichlorobenzyloxycarbonyl)-2-piperidinecarboxamido)-5-fluoro-4-oxo-pentanoic acid

EXAMPLE 13

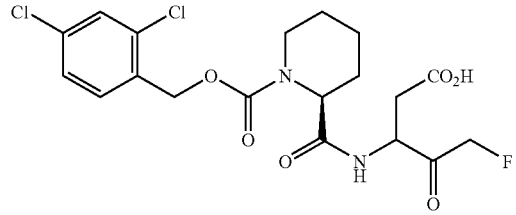

This was prepared from 2,4-dichlorobenzyl alcohol using procedures similar to those described above in Methods G, and B–E to give a white solid (80 mg, 64% last step): IR (solid) 1671, 1739, 1782 cm$^{-1}$; $^1$H NMR (400 MHz, $d_6$-DMSO) δ 1.1–1.8 (5H, m), 2.0–2.2 (1H, m), 2.5–2.9 (2H, m), 3.0–3.3 (1H, m), 3.8–4.0 (1H, m), 4.2–4.8 (2.6H, m), 5.0–5.4 (3.4H, m), 7.4–7.6 (2H, m), 7.6–7.7 (1H, m), 7.7–8.6 (1H, m); $^{13}$C NMR (100 MHz, $d_6$-DMSO) δ 22.45, 26.96, 27.10, 29.75, 30.12 ($CH_2$), 35.39, 37.15 ($CH_2$), 44.70 ($CH_2$), 49.89, 50.07, 54.63, 54.89, 57.03 (2×CH), 66.10, 66.24 ($CH_2Ar$), 84.02, 85.62, 87.61 ($CH_2F$), 130.35, 131.71, 133.77 (ArCH), 136.15, 136.18, 136.26 (ArC), 174.07, 174.14, 174.34, 174.56, 174.62, 175.81, 205.13 (CO); $^{19}$F NMR (376 MHz, $d_6$-DMSO) δ −226.7, −226.8, −226.9, −227.2, −230.2, −230.3, −230.4, −232.4, −232.6, −232.6, −232.6.

[3S/R,(2S)]-3-(1-(3,5-Dichlorobenzyloxycarbonyl)-2-piperidinecarboxamido)-5-fluoro-4-oxo-pentanoic acid

EXAMPLE 14

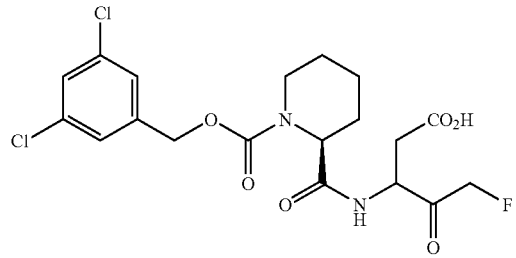

This was prepared from 3,5-dichlorobenzyl alcohol using procedures similar to those described above in Methods G, and B–E to give a white solid (95 mg, 52% last step): IR (solid) 1670, 1737, 1783 cm$^{-1}$; $^1$H NMR (400 MHz, d$_6$-DMSO) δ 1.1–1.8 (5H, m), 2.0–2.2 (1H, m), 2.4–2.9 (2H, m), 3.0–3.3 (1H, m), 3.8–4.0 (1H, m), 4.3–4.8 (2.6H, m), 4.9–5.4 (3.4H, m), 7.3–7.5 (2H, m), 7.5–7.6 (1H, m), 7.7–8.6 (1H, m); $^{13}$C NMR (100 MHz, d$_6$-DMSO) δ; $^{19}$F NMR (376 MHz, d$_6$-DMSO) δ −226.6, −226.8, −226.9, −230.0, −230.2, −230.2, −230.2, −232.5, −232.5, −232.5, −232.6.

[3S/R,(2S)]-3-(1-(2,4-Bis(trifluoromethyl)benzyloxycarbonyl)-2-piperidinecarboxamido)-5-fluoro-4-oxo-pentanoic acid

EXAMPLE 15

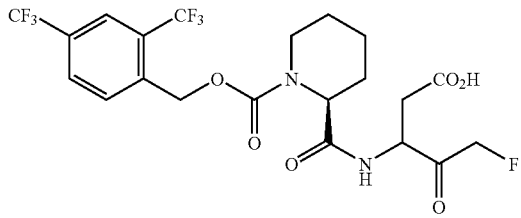

This was prepared from 2,4-bis(trifluoromethyl)benzyl alcohol using procedures similar to those described above in Methods G, and B–E to give a white solid (59 mg, 49% last step): IR (solid) 1655, 1684, 1735, 1772 cm$^{-1}$; $^1$H NMR (400 MHz, d$_6$-DMSO) δ 1.1–1.8 (5H, m), 2.0–2.2 (1H, m), 2.5–3.0 (2H, m), 3.0–3.3 (1H, m), 3.8–4.0 (1H, m), 4.2–4.8 (2.7H, m), 5.0–5.5 (3.3H, m), 7.7–8.0 (2H, m), 8.0–8.2 (1H, m), 8.2–8.6 (1H, m); $^{13}$C NMR (100 MHz, d$_6$-DMSO) δ; $^{19}$F NMR (376 MHz, d$_6$-DMSO) δ −59.88, −59.91, −61.80, −61.81, −61.84, −226.7, −226.8, −226.8, −226.9, −230.2, −230.5, −232.5, −232.7, −232.7, −232.7.

[3S/R,(2S)]-3-(1-(4-Chlorobenzyloxycarbonyl)-1,2,3,4-tetrahydro-quinolinyl-2-carboxamido)-5-fluoro-4-oxo-pentanoic acid

EXAMPLE 16

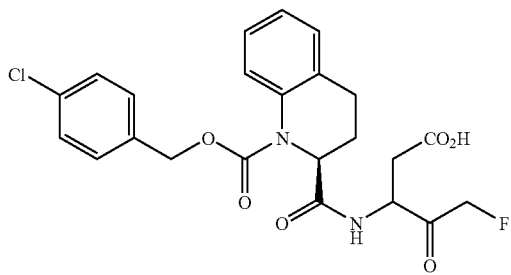

This was prepared from 4-chlorobenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester in EP 75737] using procedures similar to those described in Methods G, and B–E to produce, after reverse phase HPLC, a white solid (57.4 mg, 21%): IR (solid) 1794, 1694, 1522, 1384, 1317, 1203, 1045 cm$^{-1}$; $^1$H NMR (400 MHz, d$_6$-DMSO) δ 1.59–1.78 (1H, m), 2.20–2.40 (1H, m), 2.40–2.82 (4H, m), 4.10–5.28 (6H, m), 6.90–7.20 (3H, m), 7.31–7.48 (4H, m), 7.60–7.77 (1H, m), 8.20–8.70 (1H, m); $^{13}$C NMR (100 MHz, d$_6$-DMSO) δ 25.53, 28.01, 34.80, 52.03, 57.85, 66.63, 83.12, 84.90, 126.41, 126.45, 127.86, 128.77, 129.85, 129.93, 132.93, 135.58, 137.22 172.01, 172.07, 172.20, 202.63, 202.77; $^{19}$F NMR (376 MHz, d$_6$-DMSO) δ −226.66, −226.93, −232.77 (bm), −232.91 (bm); Low Res MS ES+ 477.131, ES− 475.20.

[3S/R,(2S)]-3-(1-(3,4-Dichlorobenzyloxycarbonyl)-1,2,3,4-tetrahydro-quinolinyl-2-carboxamido)-5-fluoro-4-oxo-pentanoic acid

EXAMPLE 17

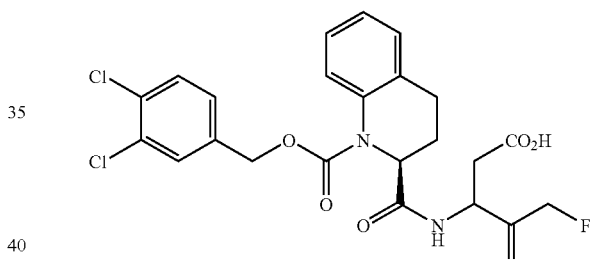

This was prepared from 3,4-dichlorobenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester described in EP 75737] using procedures similar to those described in Methods G, and B–E to produce, after reverse phase HPLC, a white solid (131.5 mg, 35%): IR (solid) 1693, 1527, 1374, 1331, 1198, 1055, 1026 cm$^{-1}$; $^1$H NMR (400 MHz, d$_6$-DMSO) δ 1.58–1.79 (1H, m), 2.19–2.39 (1H, m), 2.40–2.83 (4H, m), 4.00–5.25 (6H, m), 6.92–7.02 (1H, m), 7.05–7.21 (2H, m), 7.30–7.40 (1H, m), 7.55–7.78 (3H, m), 8.21–8.75 (1H, m); $^{13}$C NMR (100 MHz, d$_6$-DMSO) δ 24.11, 24.21, 26.58, 26.78, 26.96, 31.68, 33.18, 33.37, 50.63, 50.92, 56.41, 56.49, 56.74, 64.30, 64.52, 122.45, 124.96, 125.01, 126.37, 126.44, 126.69, 126.76, 128.44, 128.52, 129.50, 129.45, 129.99, 130.32, 135.74, 135.92, 136.29, 136.23, 152.81, 170.62, 170.65, 170.69, 170.79, 171.60, 201.19, 201.33; $^{19}$F NMR (376 MHz, d$_6$-DMSO) δ −226.75, −227.01, −232.90 (bm).

[3S/R,(2S)]-3-(1-(3-Trifluoromethylbenzyloxycarbonyl)-1,2,3,4-tetrahydro-quinolinyl-2-carboxamido)-5-fluoro-4-oxo-pentanoic acid

EXAMPLE 18

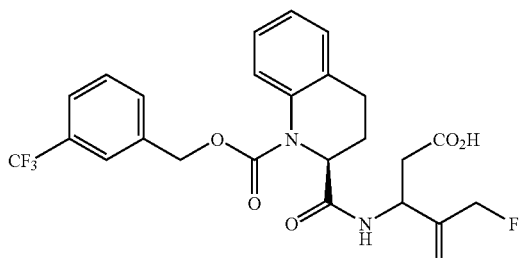

This was prepared from 3-trifluoromethylbenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester in EP 75737] using procedures similar to those described above in Methods G, and B–E to produce, after reverse phase HPLC, a white foam (69.2 mg, 30%): IR (solid) 1689, 1527, 1393, 1327, 1203, 1165, 1122 cm$^{-1}$; $^1$H NMR (400 MHz, d$_6$-DMSO) δ 1.60–1.79 (1H, m), 2.20–2.39 (1H, m), 2.40–2.80 (4H, m), 4.10–5.37 (6H, m), 6.92–7.19 (3H, m), 7.51–7.76 (4H, m), 8.19–8.74 (1H, m); $^{13}$C NMR (100 MHz, d$_6$-DMSO) δ 25.52, 25.63, 27.99, 28.20, 34.55, 34.77, 52.30, 57.84, 57.90, 66.61, 83.05, 83.27, 84.83, 85.04, 123.90, 124.31, 124.35, 124.91, 126.36, 127.75, 129.69, 131.81, 131.88, 137.17, 138.02, 138.06, 154.33, 172.02, 172.06, 172.18, 202.61, 202.75; $^{19}$FNMR (376 MHz, d$_6$-DMSO) δ –226.84, –227.08, –232.94 (bm).

[3S/R,(2S)]-5-Fluoro-3-(1-(3-methylsulphonylbenzyloxycarbonyl)-2-piperidinecarboxamido)-4-oxo-pentanoic acid

EXAMPLE 19

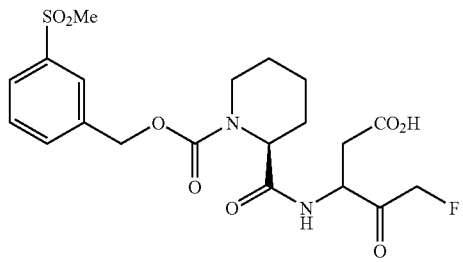

This was prepared from 3-methylsulfonylbenzyl alcohol using procedures similar to those described above in Methods G, and B–E to give a off-white solid (51.7 mg, 41% last step): IR (solid) 1676, 1733, 1787 cm$^{-1}$; $^1$H NMR (400 MHz, d$_6$-DMSO) δ 1.1–1.7 (5H, m), 2.0–2.2 (1H, m), 2.4–2.9 (3H, m), 3.1–3.3 (3H, s), 3.8–4.0 (1H, m), 4.2–4.8 (2.6H, m), 5.0–5.4 (3.4H, m), 7.6–8.0(4H, m), 8.0–8.7(1H, m); $^{13}$C NMR (100 MHz, d$_6$-DMSO) δ19.99, 24.61, 27.26, 27.65, 29.36(CH$_2$), 32.86, 34.69 (CH$_2$), 42.20(CH$_2$), 43.77 (CH$_3$), 47.41, 47.59, 52.39, 54.50 (2×CH), 65.73 (CH$_2$), 81.53, 83.30, 85.10 (CH$_2$), 125.84, 126.64, 129.99, 132.69 (ArCH), 138.89, 141.31(ArC), 171.68, 172.07, 172.13, 173.34, 202.65, 202.79(CO); $^{19}$F NMR (376 MHz, d$_6$-DMSO) δ–226.6, –226.8, –230.2, –232.4, –232.4, –232.5, –232.6.

[3S/R,(2S)]-5-Fluoro-4-oxo-3-(1-(3-phenylbenzyloxycarbonyl)-2-piperidinecarboxamido)-pentanoic acid

EXAMPLE 20

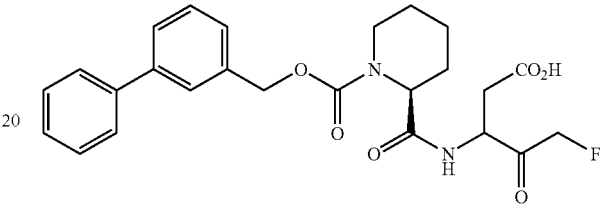

This was prepared from 3-phenylbenzyl alcohol using procedures similar to those described above in Methods G, and B–E to give a white powder (105.3 mg, 46% last step): IR (solid) 1671, 1739 cm$^{-1}$; $^1$H NMR (400 MHz, d$_6$-DMSO) δ 1.1–1.7 (5H, m), 2.0–2.2 (1H, m), 2.5–2.8 (2H, m), 3.0–3.3 (1H, m), 3.9–4.0 (1H, m), 4.2–4.8 (2.5H, m), 5.0–5.4 (3.5H, m), 7.2–7.7 (9H, m), 7.8–8.7 (1H, m); $^{13}$C NMR (100 MHz, d$_6$-DMSO) δ 20.53, 25.14, 27.63, 27.83 (CH$_2$), 33.32, 35.23 (CH$_2$), 42.68 (CH$_2$), 47.90, 48.07, 52.70, 52.89, 55.06 (2×CH), 67.20 (CH$_2$), 83.80, 85.61 (CH$_2$), 126.69, 127.04, 127.37, 127.60, 128.43, 129.82, 129.95, 131.51 (ArCH), 138.39, 138.41, 140.76, 141.18 (ArC), 172.34, 172.47, 172.59, 172.64, 203.26 (CO); $^{19}$F NMR (376 MHz, d$_6$-DMSO) δ –226.7, –226.8, –230.2, –230.3, –232.3, –232.5, –232.5, –232.6.

[3S/R,(2S)]-5-Fluoro-3-(1-(3-nitrobenzyloxycarbonyl)-2-piperidinecarboxamido)-4-oxo-pentanoic acid

EXAMPLE 21

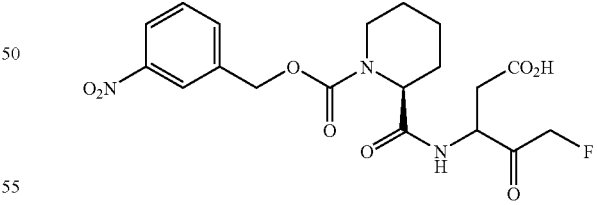

This was prepared from 3-nitrobenzyl alcohol using procedures similar to those described above in Methods G, and B–E to give a off-white solid (35.6 mg, 58% last step): IR (solid) 1671, 1739, 1786 cm$^{-1}$; $^1$H NMR (400 MHz, d$_6$-DMSO) δ 1.1–1.7 (5H, m), 2.0–2.2 (1H, m), 2.5–2.9 (2H, m), 3.0–3.3 (1H, m), 3.8–4.0 (1H, m), 4.2–4.8 (2.5H, m), 5.0–5.4 (3.5H, m), 7.6–7.9 (2H, m), 8.1–8.3 (2H, m), 8.4–8.6 (1H, m); $^{13}$C NMR (100 MHz, d$_6$-DMSO) δ 19.97, 24.46, 27.25, 27.63 (CH$_2$), 34.62 (CH$_2$), 42.20 (CH$_2$), 47.42, 52.16, 52.40, 52.51, 54.55 (2×CH), 65.47 (CH$_2$), 83.29, 85.09 (CH$_2$), 122.26, 122.30, 122.33, 123.06, 130.40, 134.29 (ArCH), 139.51, 139.55, 148.12 (ArC), 172.07 (CO); $^{19}$F NMR (376 MHz, d$_6$-DMSO) δ −226.7, −226.8, −226.9, −230.2, −230.3, −232.4, −232.6, −232.6, −232.6.

[3S/R,(2S)]-5-Fluoro-3-(1-(2,3-dichlorobenzyloxy-carbonyl)-2-piperidinecarboxamido)-4-oxo-pentanoic acid

EXAMPLE 22

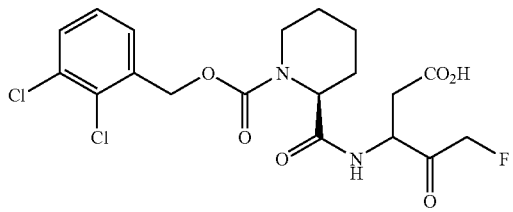

This was prepared from 2,3-dichlorobenzyl alcohol using procedures similar to those described above in Methods G, and B–E to give a off-white solid (161.2 mg, 83% last step): IR (solid) 1670, 1716, 1739, 1781 cm$^{-1}$; $^1$H NMR (400 MHz, d$_6$-DMSO) δ 1.1–1.8 (5H, m), 2.0–2.2 (1H, m), 2.5–2.9 (2H, m), 3.0–3.3 (1H, m), 3.8–4.0 (1H, m), 4.2–4.8 (2.5H, m), 5.0–5.4 (3.5H, m), 7.3–7.5 (2H, m), 7.6–7.7 (1H, m), 7.8–8.7 (1H, m); $^{13}$C NMR (100 MHz, d$_6$-DMSO) δ 20.48, 24.97, 25.14, 27.84, 28.18 (CH$_2$), 33.41, 35.20 (CH$_2$), 47.90, 48.07, 52.66, 52.90, 54.86, 55.07 (2×CH), 64.69, 65.04 (CH$_2$), 82.04, 83.83, 85.62 (CH$_2$), 128.39, 128.69, 129.19, 130.87 (ArCH), 132.67, 137.66, 137.69, 137.73, 155.58, 156.29 (ArC), 172.17, 172.36, 172.57, 172.63, 173.82, 203.28 (CO); $^{19}$F NMR (376 MHz, d$_6$-DMSO) δ −226.7, −226.8, −226.9, −230.2, −230.3, −230.4, −232.4, −232.5, −232.6, −232.6, −232.7.

[3S/R,(2S)]-5-Fluoro-3-(1-(2,5-dichlorobenzyloxy-carbonyl)-2-piperidinecarboxamido)-4-oxo-pentanoic acid

EXAMPLE 23

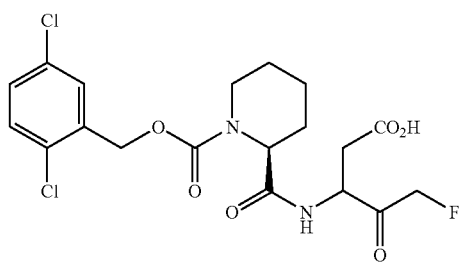

This was prepared from 2,5-dichlorobenzyl alcohol using procedures similar to those described above in Methods G, and B–E to give a pale yellow solid (114.6 mg, 71% last step): IR (solid) 1670, 1739, 1782 cm$^{-1}$; $^1$H NMR (400 MHz, d$_6$-DMSO) δ1.1–1.8 (5H, m), 2.0–2.2 (1H, m), 2.4–2.9 (2H, m), 3.0–3.4 (1H, m), 3.8–4.0 (1H, m), 4.3–4.8 (2.5H, m), 5.0–5.4 (3.5H, m), 7.3–7.6 (3H, m), 7.7–8.7 (1H, m); $^{13}$C NMR (100 MHz, d$_6$-DMSO) δ 20.48, 20.77, 24.97, 25.12, 27.61, 27.83, 29.89 (CH$_2$), 33.42, 33.50, 35.21 (CH$_2$), 42.73 (CH$_2$), 47.92, 48.11, 52.71, 52.67, 53.34, 54.88, 55.01, 55.13 (2×CH), 64.15, 64.30 (CH$_2$), 82.06, 83.81, 85.61 (CH$_2$), 129.46, 129.83, 130.05, 130.38, 131.80, 131.92 (ArCH), 132.78, 137.16, 137.19 (ArC), 171.65, 172.15, 172.35, 172.59, 173.83, 203.29 (CO); $^{19}$F NMR (376 MHz, d$_6$-DMSO) δ −226.7, −226.8, −226.9, −230.1, −230.3, −232.4, −232.5, −232.5, −232.6.

[3S/R,(2S)]-5-Fluoro-4-oxo-3-(1-(2-phenoxybenzy-loxycarbonyl)-2-piperidinecarboxamido)-pentanoic acid

EXAMPLE 24

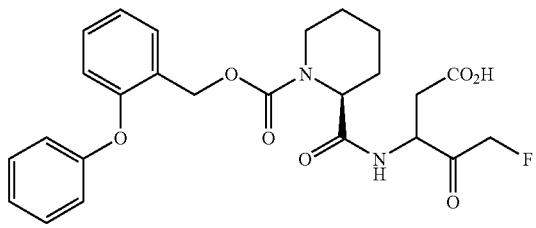

This was prepared from 3-phenoxybenzyl alcohol using procedures similar to those described above in Methods G, and B–E to give, after reverse phase HPLC, a white powder (20.0 mg, 35% last step): $^1$H NMR (400 MHz, d$_6$-DMSO) δ 1.19–1.52 (5H, m), 2.06 (1H, t), 2.56 (1H, m), 2.78 (1H, m), 2.99 (1H, m), 3.73 (1H, m), 4.29–5.20 (6H, m), 7.10–7.48 (9H, m), 8.10, 8.50 (1H, 2×d, J 8.0 Hz); $^{13}$C NMR (100 MHz, d$_6$-DMSO) δ20.01, 21.52 (CH$_2$), 24.57 (CH$_2$), 27.22, 27.60 (CH$_2$), 34.70 (CH$_2$), 41.98 (CH$_2$), 52.16, 53.38 (CH), 54.51, 56.05 (CH), 62.32 (CH$_2$), 83.30 (d, J 178 Hz, CH$_2$), 114.25 (C), 117.13 (C), 118.06 (CH), 119.38, 119.63 (CH), 123.51 (CH), 124.38 (CH), 128.24, 128.27 (C), 129.94, 130.15, 130.35 (CH), 171.63, 171.89 (CO), 172.07, 172.13 (CO); $^{19}$F NMR (376 MHz, d$_6$-DMSO) δ −226.67, −226.80, −232.43, −232.57, −232.63.

[3S/R,(2S)]-3-(1-(2-Chlorobenzyloxycarbonyl)-1,2,3,4-tetrahydro-quinolinyl-2-carboxamido)-5-fluoro-4-oxo-pentanoic acid

EXAMPLE 25

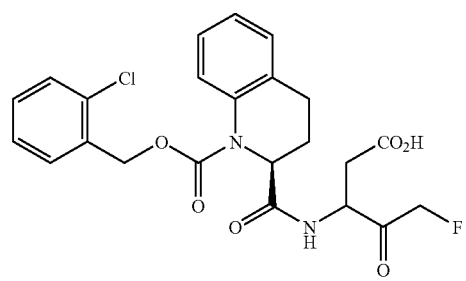

This was prepared from 2-chlorobenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester described in EP 75737] using procedures similar to those described in Methods G, and B–E to leave a colorless solid (64 mg, 99.3% last step): IR (solid) 1789.2, 1694.6, 1527.6, 1493.0, 1392.2, 1324.1, 1282.5, 1235.7, 1207.9, 1172.1, 1121.6, 1048.5, 757.3.; $^1$H NMR (400 MHz, $d_6$-DMSO) δ 1.75 (1H, m), 2.30 (1H, m), 2.44–2.88 (4H, m), 4.15–5.35 (6H, m), 7.00 (1H, m), 7.17 (2H, m), 7.39 (2H, m), 7.49 (2H, m), 7.70 (1H, m), 8.28+8.68 (1H, 2×m); $^{13}$C NMR (100 MHz, $d_6$-DMSO) δ 24.00, 24.13, 26.47, 26.71, 26.89, 33.12, 33.31 (CH2), 45.84, 50.82, 56.56 (CH), 63.12, 63.24, 63.36 (CH2), 82.59 (d, J 177, CH2F), 122.19, 122.68, 125.00, 128.76, 128.86, (CH), 130.22, 131.13, 132.35, 132.38135.64, 135.83 (C), 152.70, 170.40, 170.43, 170.55, 170.59 (C=O), 200.97, 202.10, 201.24 (FCH2C=O).); $^{19}$F NMR (376 MHz, $d_6$-DMSO) δ–226.63 (t, J 45), –226.92 (t, J 45), –230.52 (t, J 45), –232.84 (m).

[3S/R,(2S)]-3-(1-(3-Chlorobenzyloxycarbonyl)-1,2,3,4-tetrahydro-quinolinyl-2-carboxamido)-5-fluoro-4-oxo-pentanoic acid

EXAMPLE 26

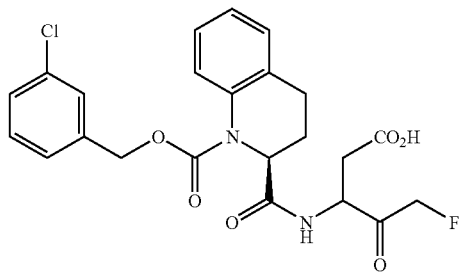

This was prepared from 3-chlorobenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester described in EP 75737] using procedures similar to those described in Methods G, and B–E to produce a colorless solid (124 mg, 99.3% last step): IR (solid) 1784.4, 1694.3, 1576.7, 1530.4, 1492.9, 1388.3, 1328.7, 1209.4, 1171.1, 1121.3, 1052.5, 938.5, 768.0.; $^1$H NMR (400 MHz, $d_6$-DMSO)δ 1.70 (1H, m), 2.33 (1H, m), 2.40–2.85 (4H, m), 4.05–5.30 (6H, m), 7.02 (1H, m), 7.18 (2H, m), 7.40 (4H, m), 7.71 (1H, m), 8.28+8.70(1H, 2×m); $^{13}$C NMR δ (100 MHz, $d_6$-DMSO)25.55, 25.67, 25.76, 28.02, 28.24, 28.33,33.04, 33.10, 34.63, 34.82 (CH2), 47.35, 52.06, 52.30, 57.82, 57.89 (CH), 84.11 (d, J 177, CH2F), 123.90, 124.14, 126.40, 126.45, 126.53, 127.63, 127.67, 127.73, 127.79, 128.23, 130.67 (CH), 133.41, 137.19, 139.05, 139.10 (C), 154.19, 154.31, 172.03, 172.07, 172.13, 173.06, 173.20 (C=O), 202.49, 202.63, 202.76 (FCH2C=O); $^{19}$F NMR (376 MHz, $d_6$-DMSO) δ –226.62 (t, J 45), –226.91 (t, J 45), –232.73 (br m).

[3S/R,(2S)]-3-(1-(2-trifluoromethylbenzyloxycarbonyl)-1,2,3,4-tetrahydro-quinolinyl-2-carboxamido)-5-fluoro-4-oxo-pentanoic acid

EXAMPLE 27

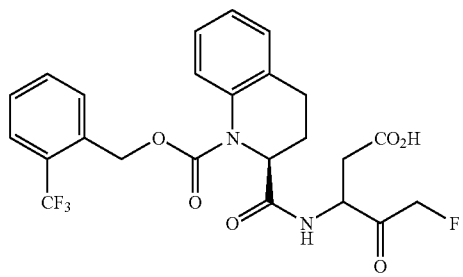

This was prepared from 2-trifluoromethylbenzyl alcohol and (S)-1-(chlorocarbonyl)-1,2,3,4-tetrahydro-quinoline-2-carboxylic acid methyl ester [prepared using a procedure similar to the one described for the synthesis of (S)-1-(chlorocarbonyl)-2-piperidinecarboxylic acid methyl ester described in EP 75737] using procedures similar to those described in Methods G, and B–E to produce a colorless solid (101 mg, 95.1% last step): IR (solid) 3308, 1694.4, 1527.1, 1493.3, 1456.7, 1398.4, 1314.9, 1209.7, 1168.5, 1118.3, 1052.8, 1039.1, 768.0 cm$^{-1}$; $^1$H NMR (400 MHz, CDCl$_3$) δ 1.99–3.20 (5H, m), 3.35–5.20 (5.5H, m), 5.30–5.50 (1.5H, m), 6.95–7.35 (6H, m), 7.44–7.78 (3H, m); $^{13}$C (100 MHz, $d_6$-DMSO) δ 25.63, 27.96, 34.80 (CH$_2$), 51.98, 57.81 (CH), 63.70 (CH$_2$), 84.08 (d, CH$_2$F, J 176), 124.58 (q, CF$_3$, J 272), 123.99, 126.29, 126.41, 126.46, 127.81, 127.94, 128.99, 129.02, 130.14 (CH), 134.55, 137.14 (C), 154.13, 171.88, 172.07, 172.12, 202.46, 202.59, 202.72 (C=O); $^{19}$F NMR (376 MHz, CDCl$_3$) –60.17 (s), –230.69 (t, J 48), –231.64 (t, J 48), –231.82 (t, J 48), –232.38 (t, J 48), –232.82 (t, J 48).

[3S/R,(2S)]-3-(1-(2-Chlorobenzyloxycarbonyl)-1,2,3,4-tetrahydro-isoquinolinyl-2-carboxamido)-5-fluoro-4-oxo-pentanoic acid

EXAMPLE 28

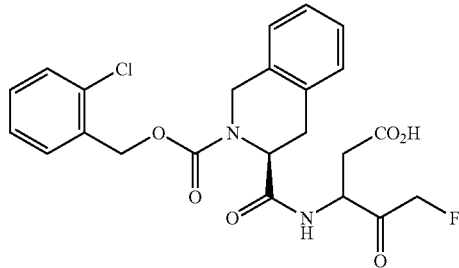

This was prepared from 2-chlorobenzyl alcohol and (S)-1-(chlorocarbonyl)-1,2,3,4-tetrahydro-isoquinoline-2-carboxylic acid methyl ester [prepared using a procedure similar to the one described for the synthesis of (S)-1-(chlorocarbonyl)-2-piperidinecarboxylic acid methyl ester described in EP 75737] using procedures similar to those described in Methods G, and B–E to produce, after reverse phase HPLC, a white foam (57.9 mg, 98% last step): IR (solid) 1793, 1680, 1516, 1404, 1337, 1209, 1122, 1055; $^1$H NMR (400 MHz, d$_6$-DMSO) δ 2.20–2.80 (2H, m, Asp), 3.00–3.21 (2H, m, CHCH2), 3.84–5.30 (8H, m, NCH2, OCH2, CH2F, 2×Ha), 7.08–7.60 (8H, M, ArH), 8.08–8.63 (1H, m, NH); $^{13}$C NMR (100 MHz, d$_6$-DMSO) δ 30.40, 30.70, 30.85, 33.10, 33.23 (CH2, CHCH2, AspCH2), 43.59, 43.71 (CH2, NCH2), 51.02, 53.17, 53.50, 53.60 (CH, Has), 62.83, 62.91, 63.05 (CH2, OCH2), 81.18, 81.39, 82.96 (CH2, CH2F), 125.86, 126.28, 126.46, 126.66, 128.12, 128.33, 128.67, (CH, ArCH), 131.65, 131.89, 132.02, 132.45, 132.90 (C, ArC), 170.29, 170.60 (C, C=O), 200.81, 200.93 (C, C=O); $^{19}$F NMR (376 MHz, d$_6$-DMSO) δ–226.80, –226.96, –227.04, –232.81, –233.10, –233.29, –233.41.

[3S/R,(2S)]-3-(1-(Benzyloxycarbonyl)-1,2,3,4-tetrahydro isoquinolinyl-2-carboxamido)-5-fluoro-4-oxo-pentanoic acid

EXAMPLE 29

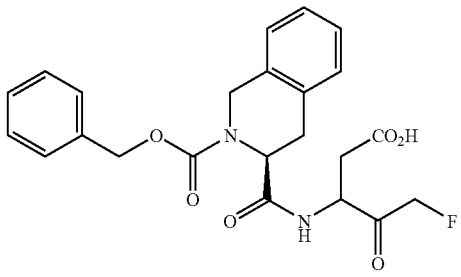

This was prepared from (S)-1-(benzyloxycarbonyl)-1,2,3,4-tetrahydro-isoquinoline-2-carboxylic acid [J. Med. Chem., (1991), 3350] using procedures similar to those described in Methods C–E to produce title compound as a yellow gum (153 mg, 100% last step): IR (solid) 1736, 1360, 1231, 1217; $^1$H NMR (400 MHz, d6-DMSO) 2.24–2.40 (1H, m), 2.57–2.69 (1H, m), 3.05–3.17 (2H, m), 4.14–4.84 (6H, m), 5.07–5.21 (2H, m), 7.20–7.44 (9H, m), 8.49–8.56 (1H, m), 12.41 (1H, br s); $^{19}$F NMR (376 MHz, d$_6$-DMSO) δ–226.7, –226.969, –227.0, –233.0, –233.0, –233.2, –233.3.

[3S/R,(2S)]-5-Fluoro-3-(1-(3-acetamidobenzyloxycarbonyl))-2-piperidinecarboxamido)-4-oxo-pentanoic acid

EXAMPLE 30

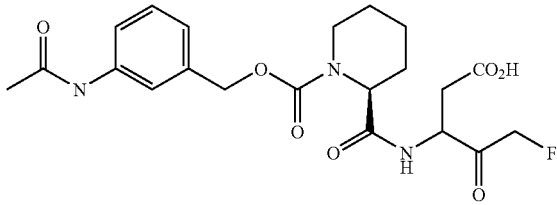

This was prepared from N-(3-hydroxymethylphenyl)acetamide using procedures similar to those described in Methods G, and B–E to give white solid (26.9 mg, 99.2% last step): IR (solid) 1666.3, 1786.9 cm-1; $^1$H NMR (400 MHz, d$_6$-DMSO) δ 1.1–1.8(5H, m, pip), 1.9–2.2(4H, m, Ac, pip), 2.4–2.9(2H, m, Asp), 3.0–3.6(1H, m, pip), 3.8–4.0 (1H, m, pip), 4.2–5.5(6H, m, Asp, pip, —CH2—, —CH2—F), 6.9–7.1(1H, m, Ar), 7.2–7.3(1H, m, Ar), 7.4–7.6(2H, m, Ar), 7.8–8.7(1H, m, NH), 9.9–10.1 (1H, br s, NH); $^{13}$C NMR (100 MHz, d$_6$-DMSO) δ 20.02(CH2, pip), 24.35 (CH3, Ac), 24.65, 27.33, 42.11(CH2, pip), 54.27, 54.52(CH, Asp, pip), 66.70(CH2, —CH2—Ar), 118.18, 118.74, 122.34, 129.10(CH, Ar), 137.62, 139.79(C, Ar), 168.71(C, C=O); $^{19}$F NMR (376 MHz, d$_6$-DMSO) δ–226.7, –232.5

[3S/R,(2S)]-5-Fluoro-3-(1-(3-methanesulfonamido) benzyloxycarbonyl)-2-piperidinecarboxamido)-4-oxo-pentanoic acid

EXAMPLE 31

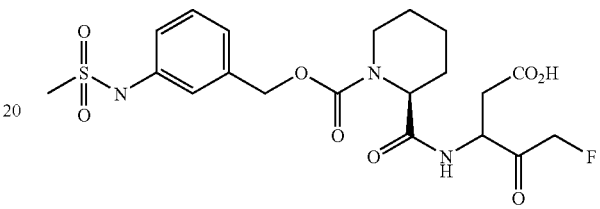

This was prepared from N-(3-hydroxy methyl-phenyl)methanesulfonamide using procedures similar to those described above in Methods G, and B–E to give white solid (35.2 mg, 98.7% last step): IR (solid) 1668.0, 1738.4 cm-1; $^1$H NMR (400 MHz, d$_6$-DMSO) δ 1.1–1.7(5H, m, pip), 2.0–2.2(1H, m, pip), 2.5–2.9(2H, m, Asp), 2.9–3.5(4H, m, pip, —SO2Me), 3.8–4.0(1H, m, pip), 4.5–5.5(6H, m, Asp, pip, —CH2—, —CH2—F), 7.0–7.4(4H, m, Ar), 8.0–8.8(1H, br s, NH), 9.6–10.0(1H, br s, NH) ; $^{13}$C NMR (100 MHz, d$_6$-DMSO) δ 20.03, 20.14, 24.66, 27.17, 27.32(CH2, pip), 39.60(CH3, —SO2Me), 42.11(CH2, pip), 54.28, 54.46(CH, Asp, pip), 66.34(CH2, —CH2—Ar), 118.44, 119.14, 122.81, 129.74(CH, Ar), 138.48, 138.92(C, Ar), 171.56(C, C=O) ; $^{19}$F NMR (376 MHz, d$_6$-DMSO) δ –232.5

[3S/R,(2S)]-5-Fluoro-4-oxo-3-(1-(3-chloro-2-thienylmethoxycarbonyl)-2-piperidinecarboxamido)-pentanoic acid

EXAMPLE 32

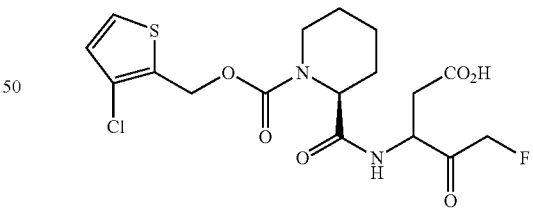

This was prepared from 3-chloro-2-thiophenemethanol using procedures similar to those described above in Methods G, and B–E to give a pale cream solid (4.4 mg, 98.7% last step): IR (Nicolet Avantar, 360 Omni Sampler, cm-1) 3316, 2951, 1677; $^1$H NMR (400 MHz, d$_6$-DMSO) δ 1.21–1.75 (5H, m, CH2pip), 2.07 (1H, m CH2pip), 2.67 (1H, m, CH2pip), 2.82–3.13 (2H, m, CH2Asp), 3.86 (1H, m, CH2), 4.57–5.26 (6H, m), 7.07 (1H, s, CHthiophene), 7.69 (1H, s, CHthiophene), 8.44 (1H, d, J 7, NH) ; $^{13}$C NMR (100 MHz, d$_6$-DMSO) δ 19.92 (CH2), 24.46 (CH2), 27.22 (CH2), 34.67 (CH2), 39.13 (CH2), 42.15 (CH2), 52.16, 52.43 (CH, a-CH), 54.53 (CH, a-CH), 59.01 (CH2), 83.25 (d, J 178, CH2F), 124.27 (C), 127.65 (CH), 131.75 (C), 171.56 171.81 (C, CO), 172.07, 172.14 (C, CO); $^{19}$F NMR (376 MHz, d$_6$-DMSO) δ −226.90, −232.39, −232.62, −232.69.

2-(1-Carboxymethyl-3-fluoro-2-oxo-propylcarbamoyl)-piperidine-1-carboxylic acid 2,2,2-trifluoro-1-naphthalen-1-yl-ethyl ester

EXAMPLE 33

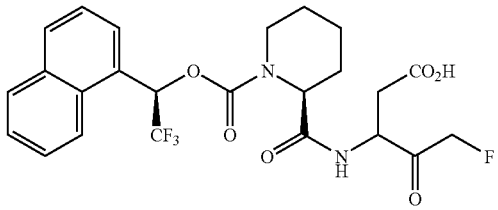

This was prepared from (R)-(−)-α-(trifluoromethyl)-naphthyl alcohol (prepared according to *Tetrahedron*, 1993, 49(9), 1725–1738) using procedures similar to those described above in Methods F, and B–E to give a white solid (176.2 mg, 98.1% last step): IR (Solid) 1712.7, 1785.8 cm-1; $^1$H NMR(400 MHz, d$_6$-DMSO) δ 1.1–1.9(5H, m, pip), 1.9–2.3(1H, m, pip), 2.5–2.9(2H, m, Asp), 3.0–3.6(1H, m, pip), 4.1–4.2(1H, m, pip), 4.3–5.3(4H, m, Asp, pip, —CH2—F), 7.0–7.1(1H, m, Ar—CH—), 7.5–8.4(7H, m, Ar), 8.4–8.8(1H, m, NH)); $^{13}$C NMR (100 MHz, d$_6$-DMSO) δ 20.31, 24.86, 25.16, 27.97, 28.25(CH2, pip), 35.22(CH2, Asp), 43.04(CH2, pip), 52.68, 52.87(CH, Asp), 55.02, 55.21 (CH, pip), 69.27, 69.57, 69.92(C, CF3), 83.88, 83.96, 85.65, 85.74(CH2, —CH2—F), 123.35(C, Ar), 124.01, 124.18, 126.09, 126.24, 126.79, 126.97, 127.09, 127.28, 127.95(CH, Ar), 128.44, 128.55, 128.94(C, Ar), 129.59, 130.94, 131.01, 131.12(C, Ar), 131.44, 131.52, 133.93, 134.06(C, Ar), 153.71, 154.40, 171.73, 171.87, 171.96, 172.54, 203.20, 203.34(C, C═O); $^{19}$F NMR (376 MHz, d$_6$-DMSO) δ−74.5, −74.6, −74.6, −74.6, −74.8, −74.9, −75.3, −226.5, −226.6, −226.8, −227.0, −230.0, −230.1, −230.2, −232.1, −5 232.5, −232.5, −232.6.

[3S/R,(2S,α-R)]-5-Fluoro-3-(1-(□-trifluoromethyl (3-chloro benzyloxycarbonyl)-2-piperidinecarboxamido)-4-oxo-pentanoic acid

EXAMPLE 34

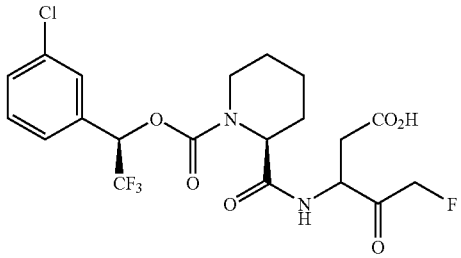

This was prepared from (R)-(−)-α-(trifluoromethyl)-3 chlorobenzyl alcohol (prepared using procedures from *Tetrahedron*, 1993, 49(9), 1725–1738)using procedures similar to those described above in Methods F, and B–E to give a white solid (101 mg, 99%): IR (Solid) 1716.1, 1782.8 cm-1; 1H NMR (400 MHz, DMSO) δ 1.1–1.8(5H, m, pip), 1.9–2.3 (1H, m, pip), 2.4–2.9(2H, m, Asp), 3.0–3.5(1H, m, pip), 3.8–4.1(1H, m, pip), 4.3–5.3(4H, m, Asp, pip, —CH2—F), 6.3–6.5(1H, m, Ar—CH—), 7.3–7.7(4H, m, Ar), 7.7–8.8 (1H, m, NH); $^{13}$C NMR (100 MHz, d$_6$-DMSO) δ 18.25, 18.34, 22.79, 23.08, 25.98, 26.06, 26.22(CH2, pip), 33.20, 33.26(CH2, Asp), 41.03(CH2, pip), 45.90, 46.03, 46.29, 50.65, 50.76, 50.92(CH, Asp), 53.07, 53.12, 53.21, 53.27, 53.44, 53.50(CH, pip), 69.87, 69.96, 70.19, 70.52(CH, CF3), 81.49, 81.85, 83.63(CH2, —CH2—F), 117.94, 120.74, 123.53(C, Ar), 125.09, 125.27, 126.35, 126.57, 128.51, 128.57, 128.68, 129.28, 129.33, 129.66(CH, Ar), 132.08, 132.18, 132.64, 132.72, 133.01(C, Ar), 151.54, 151.60, 151.68, 151.93, 152.30, 169.51, 169.72, 169.99, 170.05, 170.17, 170.49, 170.54, 170.61, 171.76, 201.02, 201.16, 201.30(C, C═O); $^{19}$F NMR (376 MHz, d$_6$-DMSO) δ −75.4, −75.4, −75.5, −75.6, −75.7, −75.7, −75.7, −75.8, −75.8, −226.6, −226.7, −226.8, −227.0, −230.0, −230.0, −230.1, −232.2, −232.5, −232.6.

[3S/R,(2S,α-R)]-5-Fluoro-3-(1-(□-pentafluoromethyl(benzyloxycarbonyl)-2-piperidinecarboxamido)-4-oxo-pentanoic acid

EXAMPLE 35

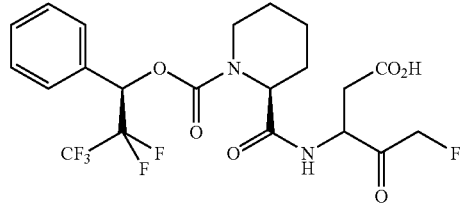

This was prepared from (R)-(−)-α-(pentafluoromethyl)-benzyl alcohol (prepared according to *Tetrahedron*, 1993, 49(9), 1725–1738) using procedures similar to those described above in Methods F, and B–E to give a white solid (59.7 mg, 99.2%); IR (Solid) 1721.1, 1736.7 cm-1; 1H NMR (400 MHz, DMSO) δ 1.1–1.8(5H, m, pip), 1.9–2.3(1H, m, pip), 2.5–2.9(2H, m, Asp), 3.0–3.5(1H, m, pip), 3.7–4.2(1H, m, pip), 4.3–5.3(4H, m, Asp, pip, —CH2—F), 6.2–6.4(1H, m, Ar—CH—), 7.3–7.6(5H, m, Ar), 7.7–8.8(1H, m, NH) ; $^{13}$C NMR, (100 MHz, d$_6$-DMSO) δ 18.14, 18.39, 22.88, 22.99, 26.05, 26.19(CH2, pip), 33.11, 33.22(CH2, Asp), 40.91, 40.95(CH2, pip), 45.85, 46.08, 46.22, 50.57, 50.64, 50.91, 50.98(CH, Asp), 52.97, 53.13, 53.31(CH, pip), 69.30, 69.39, 69.51, 69.60, 69.70, 69.90, 70.26(CH, C2F5), 79.77, 80.13, 81.52, 81.90, 83.59, 83.72 (CH2, —CH2—F), 126.96, 127.08, 127.27, 127.30, 127.54, 128.62, 128.72(CH, Ar), 129.56, 129.86(C, Ar), 151.26, 151.35, 151.61, 152.26, 169.52, 169.65, 169.81, 170.17, 170.22, 170.52, 170.63, 171.66, 171.75, 201.17, 201.31(C, C═O); $^{19}$F NMR (376 MHz, d$_6$-DMSO) δ −81.1, −81.2, −81.2, −81.2, −81.3, −81.3, −118.4 to −118.6, −119.1 to −119.3, −126.0 to −126.6, −127.0 to −127.4, −226.6, −226.8, −226.9, −227.0, −230.0, −230.2, −230.4, −232.0, −232.6, −232.8.

[3S/R,(2S,α-R)]-5-Fluoro-3-(1-(α-trifluoromethyl-benzyloxycarbonyl-1,2,3,4-tetrahydro-quinolinyl-2-carboxamido)-4-oxo-pentanoic acid

EXAMPLE 36

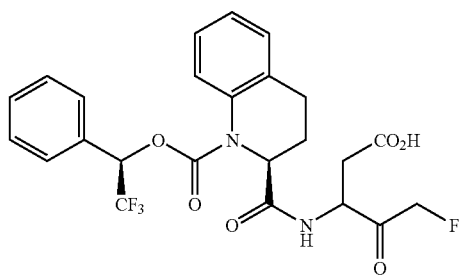

This was prepared from (R)-(−)-α-(trifluoromethyl)-benzyl alcohol using procedures similar to those described above in Methods F, and B–E to give a colorless solid (330 mg, 98.8%); IR (Solid) 3708.0, 3680.6, 2865.2, 1705.6, 1493.9, 1346.0, 1262.7, 1182.4, 1132.5, 1054.7, 1033.0, 1013.0, 703.8 cm$^{-1}$; $^1$H NMR (400 MHz, d$_6$-DMSO δ 2.28–2.85 (5H, m), 4.05–5.20 (5H, m), 6.45 (1H, m), 6.95–7.32 (3H, m), 7.38–7.75 (6H, m), 8.30–8.85 (1H, m); $^{13}$C NMR 100 MHz, d$_6$-DMSO) δ 25.66, 28.69, 34.93, (CH$_2$), 47.44, 51.84, 58.07, 72.77 (q, CHCF$_3$, J 120), 84.18 (d, CH$_2$F, J 176), 122.38, 125.17 (C), 126.55, 126.61, 127.89, 128.01, 128.07, 130.14 (CH), 136.68 (C), 171.34, 171.67, 172.01, 173.02, 202.55, 202.67, 202.97 (C=O); $^{19}$F NMR (376 MHz, d$_6$-DMSO) δ −74.21 (s), −226.62 (t, J 48), −226.99 (t, J 48), −232.67 (br m).

[3S/R,(2S,α-R)]-5-Fluoro-3-(1-(α-trifluoromethyl-(3-chlorobenzyloxycarbonyl-1,2,3,4-tetrahydro-quinolinyl-2-carboxamido)-4-oxo-pentanoic acid

EXAMPLE 37

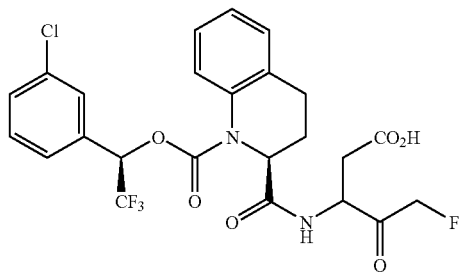

This was prepared from (R)-(−)-a-(trifluoromethyl)-3-chlorobenzyl alcohol using procedures similar to those described above in Methods F, and B–E to give a colorless solid (323 mg 99.1%); IR (solid) 3710.2, 3680.7, 2981.2, 2865.1, 1716.3, 1493.6, 1455.1, 1346.2, 1258.1, 1185.7, 1135.3, 1054.8, 1033.0, 1012.9 cm$^{-1}$; $^1$H NMR (400 MHz, d$_6$-DMSO) δ 2.20–2.83 (5H, m), 3.65–5.22 (5H, m), 5.50 (1H, m), 6.90–7.30 (3H, m), 7.35–7.75 (5H, m), 8.25–8.90 (1H, m); $^{13}$C NMR (100 MHz, d$_6$-DMSO) δ 25.64, 28.33, 33.26, 34.93 (CH$_2$), 72.23 (q, CHCF$_3$, J 120), 84.14 (d, CH$_2$F, J 176), 122.15, 124.94 (C), 126.56, 126.62, 126.66, 127.93, 127.99, 130.18, 131.00 (CH), 133.64, 133.92 (C), 171.34, 171.68, 172.00, 173.13, 202.47, 202.62, 202.67, 202.97 (C=O); $^{19}$F NMR (376 MHz, d$_6$-DMSO) δ −75.24 (s, CF$_3$), −226.66 (t, J 48), −227.00 (t, J 48), −232.39 (br m).δ

2-(1-Carbamoylmethyl-3-fluoro-2-oxo-propylcarbamoyl)-piperidine-1-carboxylic acid 3,4-dichloro-benzyl ester

EXAMPLE 38

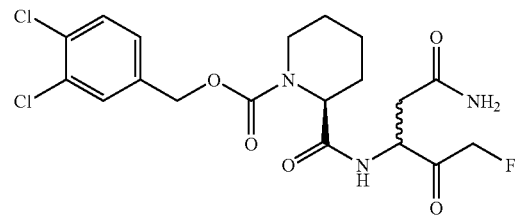

This was prepared from [3S/R,(2S)]-3-(1-(3,4-Dichlorobenzyloxycarbonyl)-2-piperidinecarboxamido)-5-fluoro-4-oxo-pentanoic acid.

Method H

Compound 38

To a stirred solution of [3S/R,(2S)]-3-(1-(3,4-Dichlorobenzyloxycarbonyl)-2-piperidinecarboxamido)-5-fluoro-4-oxo-pentanoic acid (0.2 g, 0.43 mmol) in tetrahydrofuran (THF) (2 mL) 0° C. was added N-(3-Dimethylaminopropyl)-N-ethylcarbodiimide hydrochloride. A solution of ammonia in dioxane in THF (1.29 mmol) was added to the reaction mixture after it was allowed to warm up to ambient, and the solution was stirred overnight at room temperature. The reaction mixture was concentrated in vacuo. The residue was purified by flash chromatography to give the title compound as a colorless gum (mg): $^1$H NMR (400 MHz, CDCl$_3$) δ 1.3–1.8(5H, m, pip), 2.1–2.5(2H, m, Asp-CH2, pip), 2.6–3.2 (2H, m, Asp-CH2, pip), 3.9–5.0(5H, m, Asp-CH, pip-CH, —CH2—F, NH), 5.0–5.2(2H, m, —CH2—Ar), 5.3(0.5H, m, NH), 6.6(0.4H, br s, NH), 6.8–7.1(1H, m, NH), 7.2(1H, m, Ar), 7.5(2H, m, Ar); $^{19}$F NMR (376 MHz, CDCl3) δ −225.0, −225.8, −227.6, −227.9.

2-(1-Ethylcarbamoylmethyl-3-fluoro-2-oxo-propylcarbamoyl)-piperidine-1-carboxylic acid 3,4-dichloro-benzyl ester

EXAMPLE 39

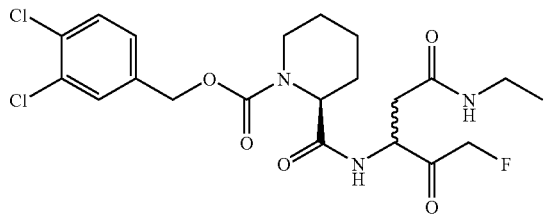

This was prepared using procedures similar to those described above in Methods H, to give a colorless gum (mg): ¹H NMR (400 MHz, CDCl₃) δ 1.2(3H, m, Et), 1.3–1.8(5H, m, pip), 2.1–2.5(2H, m, Asp-CH2, pip), 2.6–3.1(2H, m, Asp-CH2, pip), 3.1–3.5(2H, m, Et), 3.9–4.9(5H, m, Asp-CH, pip—CH, —CH2—F, NH), 5.0–5.2(2H, m, —CH2—Ar), 6.3–6.7(1H, m, NH), 7.2(1H, m, Ar), 7.4–7.5(2H, m, Ar) ¹⁹F NMR (376 MHz, CDCl3) δ −223.4, −226.6, −226.7.

2-(1-Diethylcarbamoylmethyl-3-fluoro-2-oxo-propylcarbamoyl)-piperidine-1-carboxylic acid 3,4-dichloro-benzyl ester

EXAMPLE 40

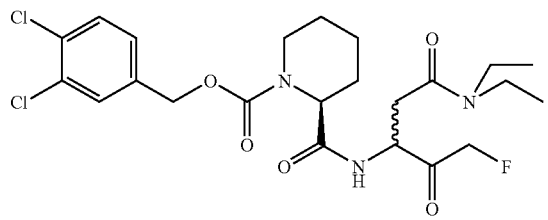

This was prepared using procedures similar to those described above in Methods H, to give a colorless gum (mg): ¹H NMR (400 MHz, CDCl₃) δ 1.0–1.3(6H, m, Et), 1.3–1.8 (5H, m, pip), 2.2–2.3(1H, m, pip), 2.7–3.2(2H, m, Asp-CH2), 3.2–3.4(4H, m, Et), 4.0–4.3(1H, m, pip), 4.7–5.4(6H, m, —CH2—F, Asp-CH, pip-CH, —CH2—Ar), 7.2(1H, m, Ar), 7.3–7.5(2H, m, Ar); ¹⁹F NMR (376 MHz, CDCl3) δ −232.3, −232.5, −232.9.

2-{1-[(2-Dimethylamino-ethylcarbamoyl)-methyl]-3-fluoro-2-oxo-propylcarbamoyl}-piperidine-1-carboxylic acid 3,4-dichloro-benzyl ester

EXAMPLE 41

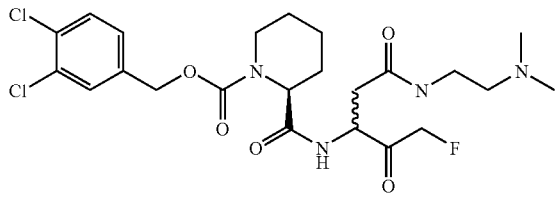

This was prepared using procedures similar to those described above in Methods H, to give a colorless gum (mg): ¹H NMR (400 MHz, CDCl3) δ 1.3–1.8(5H, m, pip), 2.1–2.4 (9H, m, —CH2—CH2—N(Me)2), 2.6(1H, m, —CH2—CH2—N(Me)2), 2.7–3.1(3H, m, Asp-CH2, pip), 4.0–4.4 (4H, m, —CH2—F, Asp-CH, pip), 4.6–4.7(1H, m, pip-CH), 4.8–4.9(1H, br s, NH), 5.0–5.2(2H, m, —CH2—Ar), 6.6–6.7(1H, m, NH), 7.2(1H, m, Ar), 7.5(2H, m, Ar); ¹⁹F NMR (376 MHz, CDCl3) δ −222.4.

2-{3-Fluoro-1-[2-(4-methyl-piperazin-1-yl)-2-oxo-ethyl]-2-oxo-propylcarbamoyl}-piperidine-1-carboxylic acid 3,4-dichloro-benzyl ester

EXAMPLE 42

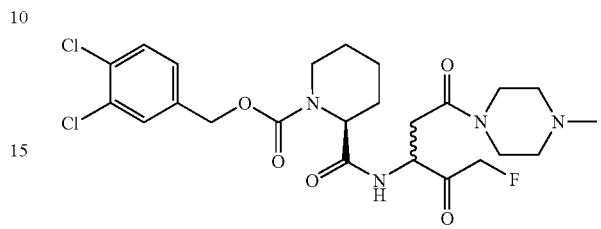

This was prepared using procedures similar to those described above in Methods H, to give a colorless gum (mg): ¹H NMR (400 MHZ, CDCl₃) δ 1.3–1.9(5H, m, pip), 2.2–2.5 (8H, m, pip), 2.7–3.2(2H, m, Asp-CH2), 3.2–3.3(1H, m, pip), 3.4–3.6(3H, m, pip), 3.6–3.7(1H, m, pip), 4.0–4.3(1H, m, pip), 4.7–5.4(6H, m, Asp-CH, pip—CH, —CH2—Ar, —CH2—F), 7.2(1H, m, Ar), 7.5(2H, m, Ar); ¹⁹F NMR (376 MHz, CDCl3) δ −233.5, −233.6, −234.0.

[3S/R,(2S)]-3-(1-(3,4-Dichlorobenzyloxycarbonyl)-2-piperidinecarboxamido)-5-fluoro-4-oxo-pentanoate, N-(4-hydroxy-2-isopropyldisulfanyl-1-methyl-butene)-N-methylformamide ester

EXAMPLE 43

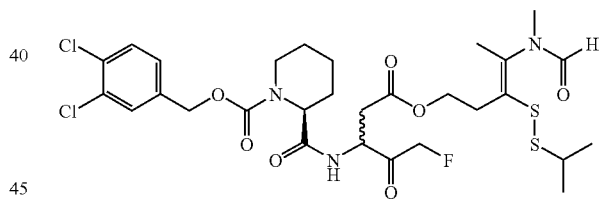

This was prepared using procedures similar to those described above in Methods H from [3S/R,(2S)]-3-(1-(3,4-Dichlorobenzyloxycarbonyl)-2-piperidinecarboxamido)-5-fluoro-4-oxo-pentanoic acid and N-(4-hydroxy-2-isopropyldisulfanyl-1-methyl-butene)N-methylformamide (Int. J. Pharmaceutics, (1995), 116, 51) to give colorless gum (159_mg, 53%): ¹H NMR (400 MHz, CDCl3) δ 1.1–1.8 (11H, m, pip, iPr), 1.8–2.1(3H, m, N-Me), 2.2–2.3(1H, m, pip), 2.7–3.3(9H, m, iPr, —O—CH2—CH2—, Asp-CH2, pip), 4.0–4.3(3H, m, pip, —O—CH2—CH2—), 4.7–5.2 (6H, m, —CH2—Ar, —CH2—F, pip, Asp), 6.9–7.1(1H, m, NH), 7.2–7.3(1H, m, Ar), 7.4–7.5(2H, m, Ar), 7.9–8.0(1H, br s, CHO); ¹⁹F NMR (376 MHz, CDCl3) δ −231.6, −231.7, −231.9.

[3S/R,(2S)]-3-(1-(5-Chloro-2-fluorobenzyloxycarbo-
nyl)-2-piperidinecarboxamido)-5-fluoro-4-oxo-pen-
tanoic acid

EXAMPLE 44

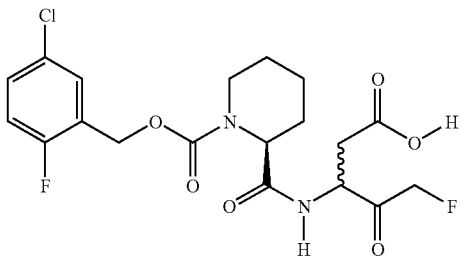

This was prepared from 5-chloro-2-fluorobenzyl alcohol using procedures similar to those described above in Methods G, and B–E to give a white foam (7.5 mg, 99% last step): IR (solid) 1788, 1670, 1491, 1424, 1404, 1250, 1178 cm-1 cm$^{-1}$; $^1$H NMR (400 MHz, d$_6$-DMSO+TFA) 1.06–1.77 (5H, m), 1.95–2.20 (1H, m), 2.28–3.30 (3H, m), 3.75–4.00 (1H, m), 4.20–4.76 (2.5H, m), 4.95–5.35 (3.5H, m), 7.18–7.35 (1H, m), 7.37–7.60 (2H, m), 8.02–8.61 (1H, m); $^{13}$C NMR (100 MHz, d$_6$-DMSO) 19.94, 20.22, 24.43, 24.56, 27.08, 27.28, 27.65, 28.82, 32.87, 34.69, 42.16, 47.38, 47.52, 52.16, 52.38, 54.44, 54.52, 60.37, 60.55, 81.44, 81.51, 83.20, 83.26, 85.03, 103.94, 104.13, 117.47, 117.59, 117.70, 117.78, 126.18, 126.34, 128.57, 128.60, 129.99, 130.22, 155.19, 155.84, 158.01, 158.14, 158.52, 158.89, 160.47, 171.14, 171.68, 171.85, 172.08, 172.13, 173.31, 202.55, 202.68; $^{19}$F NMR (376 MHz, d$_6$-DMSO+TFA) 67 −120.74, −120.85, −120.89, −120.96, −121.02, −226.68(t), −226.86 (t), −226.95(t), −230.17(t), −230.44(t), −232.51(t), −232.58 (t), −232.61(t), −232.64(t).

Enzyme Assays

The assays for caspase inhibition are based on the cleavage of a fluorogenic substrate by recombinant, purified human Caspases -1, -3, or -8. The assays are run in essentially the same way as those reported by Garcia-Calvo et al. (*J. Biol. Chem.* 273 (1998), 32608–32613), using a substrate specific for each enzyme. The substrate for Caspase-1 is Acetyl-Tyr-Val-Ala-Asp-amino-4-methylcoumarin (SEQ ID NO:1). The substrate for Caspases -3, and -8 is Acetyl-Asp-Glu-Val-Asp-amino-4-methylcoumarin (SEQ ID NO:2).

The observed rate of enzyme inactivation at a particular inhibitor concentration, k$_{obs}$, is computed by direct fits of the data to the equation derived by Thornberry et al. (*Biochemistry* 33 (1994), 3943–3939) using a nonlinear least-squares analysis computer program (PRISM 2.0; GraphPad software). To obtain the second order rate constant, k$_{inact}$, k$_{obs}$ values are plotted against their respective inhibitor concentrations and k$_{inact}$ values are subsequently calculated by computerized linear regression.

Table 2 shows a comparison between compounds of Examples 3 and 34 of this invention, and Cbz-Pro-Asp-fmk (WO 91/15557), Cbz-Thz-Asp-fmk (WO 99/477154) and 4-ClCbz-Val-Asp-fmk (WO 00/61542):

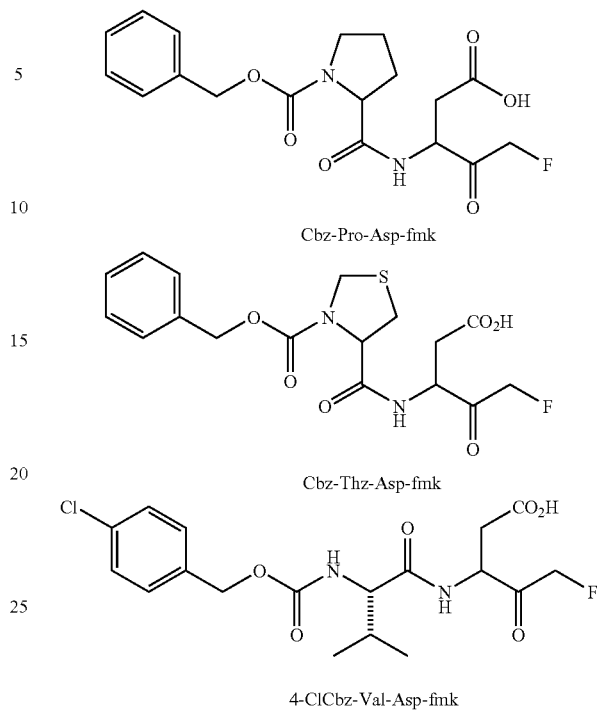

Cbz-Pro-Asp-fmk

Cbz-Thz-Asp-fmk

4-ClCbz-Val-Asp-fmk

TABLE 2

| | C-1, C-3, and C-8 Activity | | |
| --- | --- | --- | --- |
| | Kinact (x 1000 M$^{-1}$s$^{-1}$) | | |
| No. | C-1 | C-3 | C-8 |
| Example 3 | 318 | 239.5 | 122 |
| Example 34 | 518 | 181 | 839 |
| Cbz-Pro-Asp-fmk | 7.5 | 41.5 | 15.5 |
| Cbz-Thz-Asp-fmk | 227.5 | 12.5 | 12 |
| 4-ClCbz-Val-Asp-fmk | 69 | 50.5 | 175 |

As can be seen from the results in Table 2, the compounds of Example 3 and Example 34 have better activity than Cbz-Pro-Asp-fmk, Cbz-Thz-Asp-fmk and 4-ClCbz-Val-Asp across the range of caspases tested.

Inhibition of IL-1β secretion from Mixed Population of Peripheral Blood Mononuclear Cells (PBMC)

Processing of pre-IL-1β by caspase-1 can be measured in cell culture using a variety of cell sources. Human PBMC obtained from healthy donors provides a mixed population of lymphocyte and mononuclear cells that produce a spectrum of interleukins and cytokines in response to many classes of physiological stimulators.

Experimental Procedure

The test compound is dissolved in Dimethyl Sulphoxide (DMSO,Sigma #D-2650) to give a 100 mM stock solution. This is diluted in complete medium consisting of RPMI containing 10% heat inactivated FCS (Gibco BRL #10099-141), 2 mM L-Glutamine (Sigma, #G-7513), 100U penicillin and 100 µg/ml streptomycin (Sigma #P-7539). The final concentration range of test compound is from 100 µM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17-1440-02) and the cellular assay is performed in a sterile 96 well flat-bottomed plate (Nunc). Each well contains 100 μl of the cell suspension, $1\times10^5$ cells, 50 μl of compound dilutions and 50 μl of LPS (Sigma #L-3012) at 50 ng/ml final concentration. Controls consist of cells +/−LPS stimulation and a serial dilution of DMSO diluted in the same way as compound. The plates are incubated for 16–18 h at 37° C. in 5% $CO_2$ & 95% humidity atmosphere.

After 16–18 h the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600–1500 pg/ml are observed for PBMCs in positive control wells.

The inhibitory potency of the compounds can be represented by an $IC_{50}$ value, which is the concentration of inhibitor at which 50% of the mature IL-1β is detected in the supernatant as compared to the positive controls. Table 3 shows the inhibition of IL-1β secretion from PBMC for the compounds of Example 3 and Example 5 and the known Cbz-Pro-Asp-fmk and Cbz-Thz-Asp-fmk.

TABLE 3

Inhibition of IL-1β secretion from PBMC

| No. | $IC_{50}$ (nM) |
| --- | --- |
| Example 3 | 1150 |
| Example 5 | 500 |
| Cbz-Pro-Asp-fmk | >10000 |
| Cbz-Thz-Asp-fmk | 2308 |

As can be seen from the results in Table 3, the compounds of Example 3 and Example 5 provide much better inhibition of IL-1β secretion from PBMC than does Cbz-Pro-Asp-fmk or Cbz-Thz-Asp-fmk.

Hypoxia-induced Apoptosis of Cortical Neurons Assay

Caspases have been shown to significantly contribute to neuronal cell damage in a number of neurological disorders (Drug News Persp., (2000), 13(1), 5–11). Apoptosis can be induced by growth factor withdrawal and by hypoxia. This assay measures the extent of DNA fragmentation indicating the effectiveness of caspase inhibitors to prevent apoptosis.

Experimental Procedure

Cortical neurons were dissociated from Wistar rat embryos (E17) by a modification of the procedure of Rogers et al 1997, Brain Res Bulletin 44:131. Cerebral cortices were isolated aseptically from 15–20 Wistar rat embryos. A cell suspension was prepared by mincing the cerebral cortices and digesting them with papain. Cells were washed with ovomucoid enzyme inhibitor and DNaseI and plated onto Poly D lysine coated plates in high glucose DMEM containing 10% heat-inactivated foetal calf serum, L-glutamine, penicillin and streptomycin. The yield of neurons was $10^7$ per embryo and they were 80–90% viable as assessed by Trypan blue exclusion.

Cells were seeded at $1\times10^6$ cells per $cm^2$ in 96-well plates and cultured in complete medium (in high glucose DMEM containing 10% heat-inactivated foetal calf serum, L-glutamine, penicillin and streptomycin) at 37° C. in a normal atmosphere for 48 hours prior to the hypoxia experiments. Hypoxia was performed as described (Tamatani et al.1998, Molecular Brain Research, 58:27). The normal cell medium was replaced by hypoxic medium and cells were incubated in an atmosphere of 95% $N_2$/5% $CO_2$ for 42 hours. For compound testing, compounds were dissolved in DMSO at 100 mM then diluted in medium and added to the culture at the beginning of the hypoxic period. Apoptosis was measured using an ELISA assay to detect DNA fragmentation (Roche). Controls included cells cultured in aerobic conditions in serum-containing medium. Table 4 shows the activity of the compounds of Example 34 and Example 23 and the known Cbz-Pro-Asp-fmk, Cbz-Thz-Asp-fmk and 4-ClCbz-Val-Asp-fmk in the hypoxia induced apoptosis of cortical neurons assay

TABLE 4

Activity in the hypoxia induced apoptosis of cortical neurons assay

| No. | $IC_{50}$ (nM) |
| --- | --- |
| Example 34 | 463 |
| Example 23 | 336 |
| Cbz-Pro-Asp-fmk | 2776 |
| Cbz-Thz-Asp-fmk | 1563 |
| 4-ClCbz-Val-Asp-fmk | 1983 |

As can be seen from the results in Table 4, the compounds of Example 34 and Example 23 are much more potent than Cbz-Pro-Asp-fmk, Cbz-Thz-Asp-fmk and 4-ClCbz-Val-Asp-fmk in the hypoxia induced apoptosis of cortical neurons assay.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A compound of formula I:

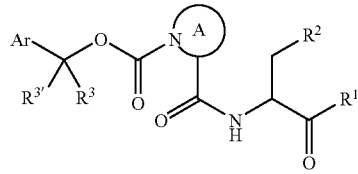

I wherein:
Ring A is an optionally substituted tetrahydroquinoline or tetrahydroisoquinoline ring;
$R^1$ is —H, —$CHN_2$, —R, or —$CH_2Y$;
R is an optionally substituted group selected from an aliphatic group, an aryl group, an aralkyl group, a heterocyclic group, or an heterocyclylalkyl group;
Y is an electronegative leaving group;
$R^2$ is $CO_2H$, $CH_2CO_2H$, or esters, amides or isosteres thereof;
Ar is an optionally substituted aryl group; and
$R^{3'}$ is —H, and $R^3$ is —H, an optionally substituted $C_{1-6}$ alkyl, CN, or aryl;
  or $R^3$ is attached to Ar to form an unsaturated or partially saturated five or six membered fused ring having 0–2 heteroatoms; or
$R^{3'}$ and $R^3$ are each —F.

2. The compound of claim 1, wherein $R^1$ is $CH_2F$.

3. The compound of claim 2 having the following features: (a) $R^1$ is $CH_2F$; (b) $R^2$ is $CO_2H$ or esters, amides or isosteres thereof; and (c) $R^3$ is hydrogen or an optionally substituted $C_{1-6}$ alkyl.

4. The compound of claim 3 where Ring A is a tetrahydroquinoline ring.

5. The compound of claim 3 where Ring A is a tetrahydroisoquinoline ring.

6. A compound, wherein the compound is

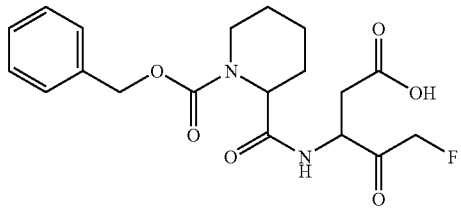

1

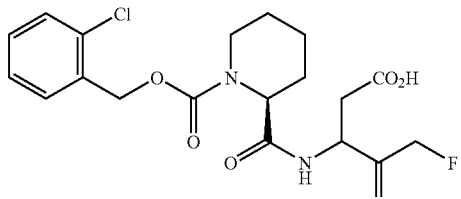

2

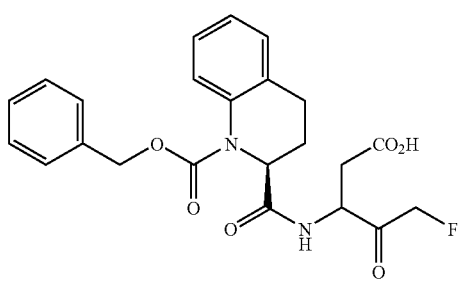

3

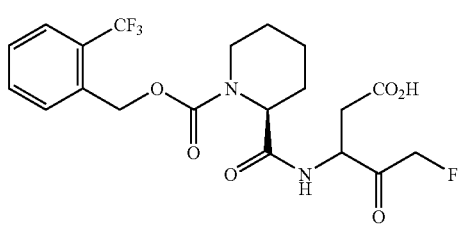

4

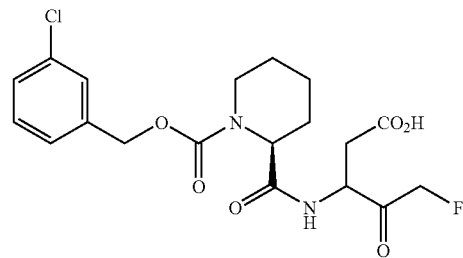
5
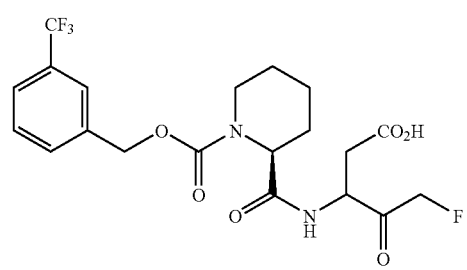
6
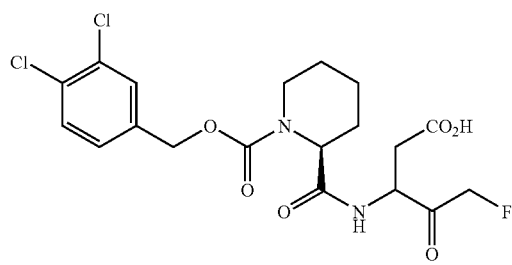
7
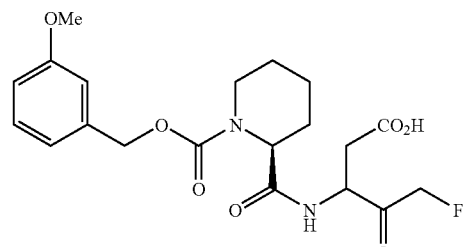
8
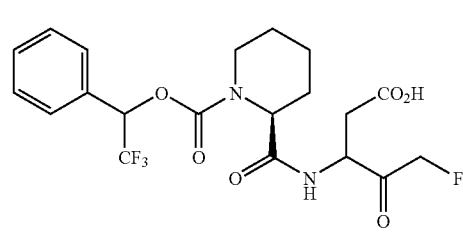
9
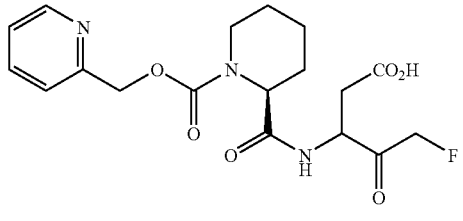
10
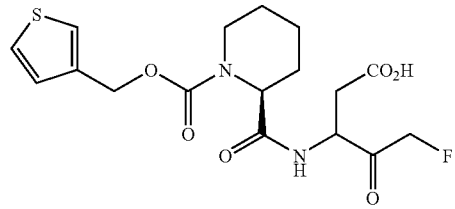
11
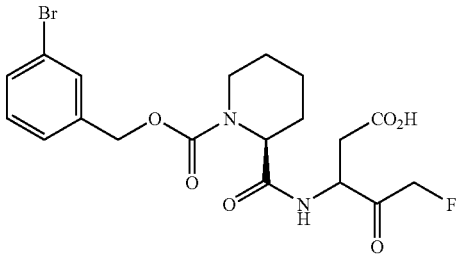
12
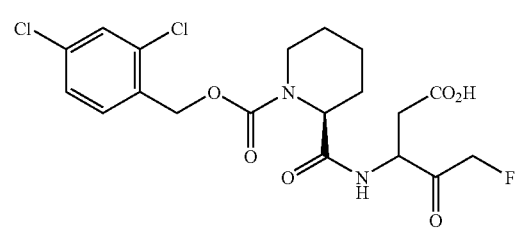
13
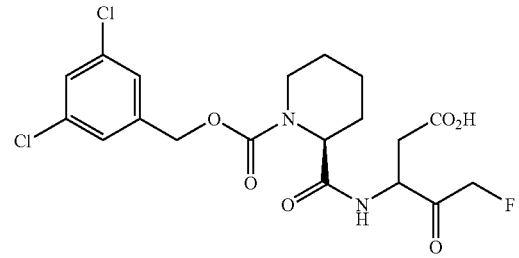
14
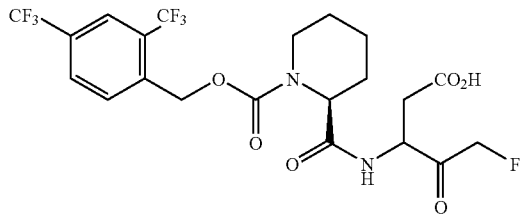
15
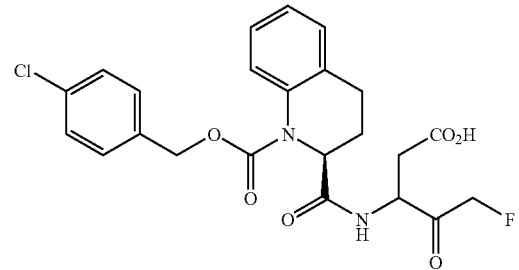
16

-continued
17
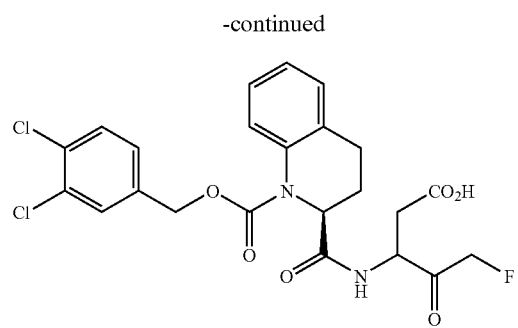
18
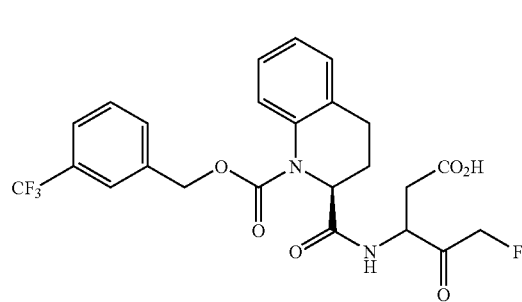
19
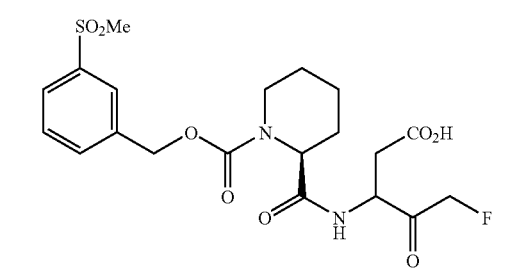
20
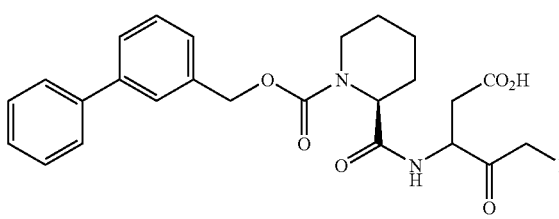
21
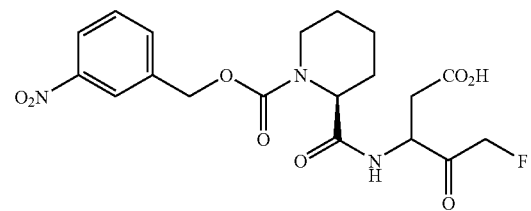
22
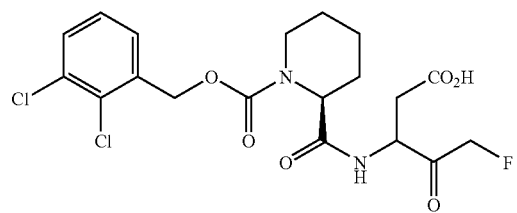
-continued
23
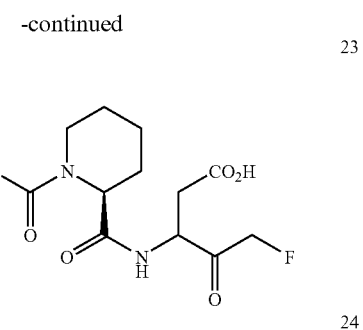
24
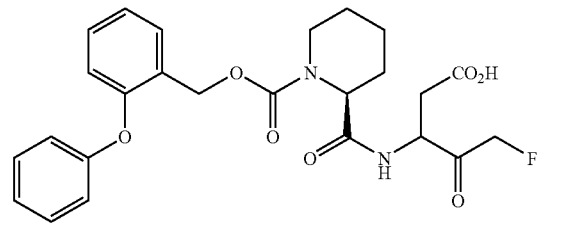
25
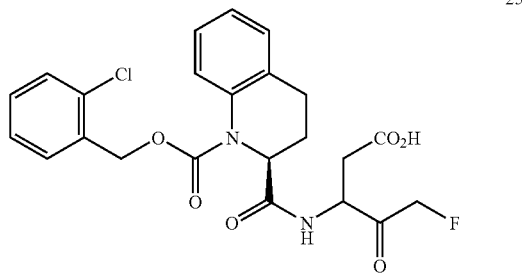
26
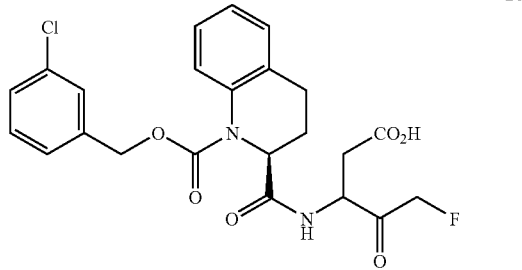
27
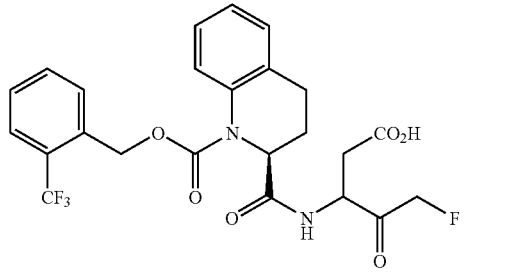
28
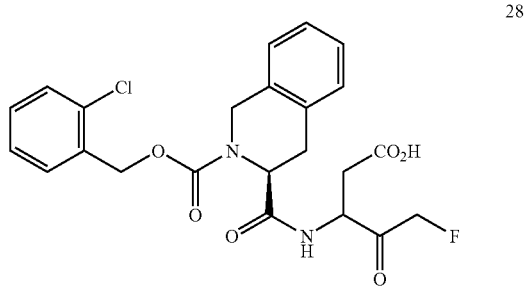

-continued

-continued

41
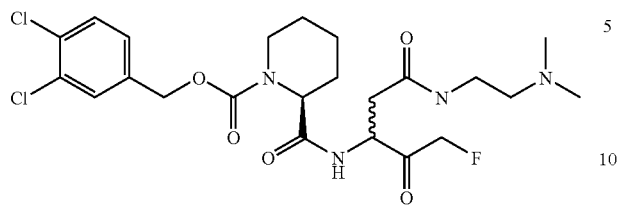

42
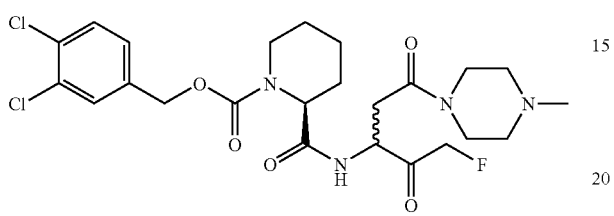

43
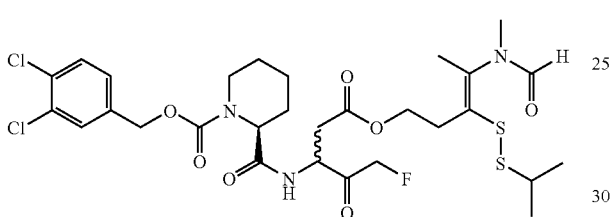

or

44
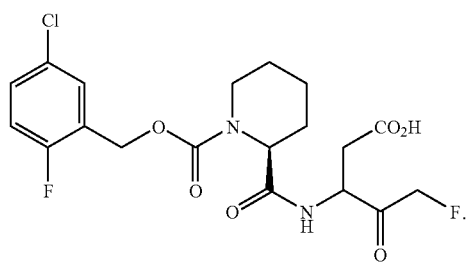

7. The compound of claim 1 where Ring A is a tetrahydroquinoline ring.

8. The compound of claim 1 where Ring A is a tetrahydroisoquinoline ring.

9. The compound of claim 1, wherein $R^2$ is $CO_2H$ or esters, amides or isosteres thereof.

10. The compound of claim 9, wherein $R^1$ is $CH_2F$.

11. The compound of claim 1, wherein $R^3$ is hydrogen or an optionally substituted $C_{1-6}$ alkyl.

12. The compound according to claim 1, wherein $R^3$ is $C_{1-6}$ haloalkyl.

13. The compound according to claim 12, wherein $R^3$ is $CF_3$.

14. The compound according to claim 12, wherein $R^3$ is $C_2F_5$.

15. The compound of claim 11, wherein $R^1$ is $CH_2F$.

16. The compound of claim 11, wherein $R^2$ is $CO_2H$ or esters, amides or isosteres thereof.

17. A compound of formula I:

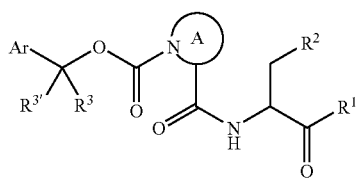

I wherein:
Ring A is an optionally substituted piperidine ring;
$R^1$ is —H, —$CHN_2$, —R, or —$CH_2Y$;
R is an optionally substituted group selected from an aliphatic group, an aryl group, an aralkyl group, a heterocyclic group, or an heterocyclylalkyl group;
Y is an electronegative leaving group;
$R^2$ is $CO_2H$, $CH_2CO_2H$, or esters, amides or isosteres thereof;
Ar is an optionally substituted aryl group; and
$R^{3'}$ is —H, and $R^3$ is —H, an optionally substituted $C_{1-6}$ alkyl, CN, or aryl;
or $R^3$ is attached to Ar to form an unsaturated or partially saturated five or six membered fused ring having 0–2 heteroatoms;
or $R^3$ and $R^{3'}$ are each —F; provided that $R^1$ is not —$CH_2$— tetrazolyl, wherein the tetrazole ring is optionally substituted.

18. A compound of formula I:

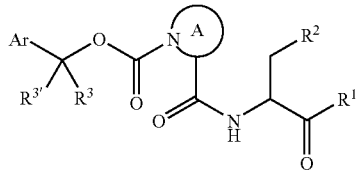

I wherein:
Ring A is an optionally substituted piperidine ring;
$R^1$ is hydrogen, $CHN_2$, or —$CH_2Y$;
Y is F, Cl, Br, I, —$OSO_2$aryl, —$OSO_2C_{1-6}$ alkyl, —$OSO_2CF_3$, —OR', —SR', —OC=O(R'), or —OPO($R^4$)($R^5$);
$R^2$ is $CO_2H$, $CH_2CO_2H$, or esters, amides or isosteres thereof;
Ar is an optionally substituted aryl group;
$R^{3'}$ is —H, and $R^3$ is —H, an optionally substituted $C_{1-6}$ alkyl, CN, or aryl;
or $R^3$ is attached to Ar to form an unsaturated or partially saturated five or six membered fused ring having 0–2 heteroatoms;
or $R^3$ and $R^{3'}$ are each —F;
$R^4$ and $R^5$ are independently —R' or —OR'; and
R' is an aliphatic group, an aryl group, an aralkyl group, a carbocyclic group, an alkyl carbocyclic group, a heterocyclic group, or an alkyl heterocyclic group, wherein each group is optionally substituted.

19. A compound of formula I:

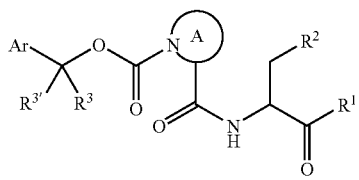

wherein:
Ring A is an optionally substituted piperidine ring;
R¹ is hydrogen, CHN₂, R, or —CH₂Y;
R is an unsubstituted aliphatic group, an optionally substituted aryl group, an optionally substituted heterocyclic group, or an optionally substituted heterocyclylalkyl group, provided that the heterocyclic group and the heterocyclylalkyl group is not aromatic;
Y is F, Cl, Br, I, —OSO₂aryl, —OSO₂C₁₋₆ alkyl, —OSO₂CF₃, —OR', —SR', —OC=O(R'), or —OPO(R⁴)(R⁵);
R² is CO₂H, CH₂CO₂H, or esters, amides or isosteres thereof;
Ar is an optionally substituted aryl group;
R³' is —H, and R³ is —H, an optionally substituted C₁₋₆ alkyl, CN, or aryl;
or R³ is attached to Ar to form an unsaturated or partially saturated five or six membered fused ring having 0–2 heteroatoms;
or R³ and R³' are each —F;
R' is an aliphatic group, an aryl group, an aralkyl group, a carbocyclic group, a carbocyclylalkyl group, a heterocyclic group, or an heterocyclylalkyl, wherein each group is optionally substituted; and
R⁴ and R⁵ are independently —R' or —OR'.

20. A compound of formula I:

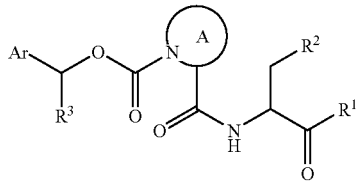

wherein:
Ring A is an optionally substituted piperidine ring;
R¹ is —H, —CHN₂, —R, or —CH₂Y;
R is an optionally substituted group selected from an aliphatic group, an aryl group, an aralkyl group, a heterocyclic group, or an heterocyclylalkyl group;
Y is an electronegative leaving group;
R² is CO₂H, CH₂CO₂H, or esters, amides or isosteres thereof;
Ar is an optionally substituted aryl group; and
R³ is a C₁₋₆ haloalkyl.

21. The compound according to claim 20, wherein R³ is CF₃.

22. The compound according to claim 20, wherein R³ is C₂F₅.

23. The compound according to claim 18, wherein R¹ is —H.

24. The compound according to claim 18, wherein R¹ is —CH₂F.

25. The compound of claim 18, wherein R¹ is —CH₂OR'.

26. The compound of claim 18, wherein R² is CO₂H or esters, amides or isosteres thereof.

27. The compound of claim 26, wherein R¹ is CH₃F.

28. The compound of claim 18, wherein R³ is hydrogen or an optionally substituted C₁₋₆ alkyl.

29. The compound of claim 28, wherein R¹ is CH₂F.

30. The compound of claim 28, wherein R² is CO₂H or esters, amides or isosteres thereof.

31. The compound of claim 30, wherein R¹ is CH₃F.

32. A method for treating a condition or disease state in mammals that is alleviated by treatment with a caspase inhibitor, comprising administering to a mammal in need of such a treatment a therapeutically effective amount of a compound according to any one of claims 1–3, 4–6 or 7–31.

33. The method of claim 32 wherein the disease is selected from an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia, epilepsy, myocardial, ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, Japanese encephalitis, liver disease, alcoholic hepatitis, renal disease, polyaptic kidney disease, H. pylori-associated gastric and duodenal ulcer disease, HIV infection, tuberculosis, and meningitis.

34. The method of claim 32 wherein the compound is used to treat complications associated with coronary artery bypass grafts.

35. A method for the preservation of cells, said method comprising the step of bathing the cells in a solution of a compound according to any one of claims 1–3, 4–6, or 7–31.

36. The method of claim 35, wherein the cells are in an organ for use in an organ transplant or in a blood product.

37. The method of claim 32 wherein the compound is used as a component of immunotherapy for the treatment of cancer.

38. A pharmaceutical composition comprising a compound according to any of claims 1–3, 4–6, or 7–31 and a pharmaceutically acceptable carrier.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:amino acid

```
        sequence substituted at the N-terminal with acetyl and at the
        C-terminal with amino-4-methyl coumarin

<400> SEQUENCE: 1

Tyr Val Ala Asp
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:amino acid
        sequence substituted at the N-terminal with acetyl and at the
        C-terminal with amino-4-methyl coumarin

<400> SEQUENCE: 2

Asp Glu Val Asp
  1
```